United States Patent
Park et al.

(10) Patent No.: US 12,180,252 B2
(45) Date of Patent: Dec. 31, 2024

(54) PEPTIDE DERIVED FROM PEP27 PEPTIDE AND USES THEREOF

(71) Applicant: INDUSTRY ACADEMIC COOPERATION FOUNDATION CHOSUN UNIVERSITY, Gwangju (KR)

(72) Inventors: Yoon Kyung Park, Jeollanam-do (KR); Hee Kyoung Kang, Gwangju (KR)

(73) Assignee: INDUSTRY ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 0 days.

(21) Appl. No.: 18/210,179

(22) Filed: Jun. 15, 2023

(65) Prior Publication Data
US 2023/0303638 A1    Sep. 28, 2023

Related U.S. Application Data

(62) Division of application No. 17/588,736, filed on Jan. 31, 2022, now abandoned.

(30) Foreign Application Priority Data
Feb. 1, 2021    (KR) .................. 10-2021-0014180

(51) Int. Cl.
| | | |
|---|---|---|
| C07K 14/315 | (2006.01) | |
| A23K 20/147 | (2016.01) | |
| A23L 33/18 | (2016.01) | |
| A61K 8/64 | (2006.01) | |
| A61P 31/04 | (2006.01) | |
| A61Q 19/00 | (2006.01) | |
| A61Q 19/10 | (2006.01) | |
| A61K 38/00 | (2006.01) | |

(52) U.S. Cl.
CPC ........ *C07K 14/3156* (2013.01); *A23K 20/147* (2016.05); *A23L 33/18* (2016.08); *A61K 8/64* (2013.01); *A61P 31/04* (2018.01); *A61Q 19/007* (2013.01); *A61Q 19/10* (2013.01); *A23V 2002/00* (2013.01); *A61K 38/00* (2013.01)

(58) Field of Classification Search
CPC .............. C07K 14/3156; A23K 20/147; A23L 33/18; A61K 8/64; A61K 38/00; A61P 31/04; A61Q 19/007; A61Q 19/10; A61Q 17/005; A23V 2002/00; C12R 2001/46
See application file for complete search history.

(56) References Cited

PUBLICATIONS

Gisele Rodrigues, Bacterial Proteinaceous Compounds With Multiple Activities Toward Cancers and Microbial Infection, Front. Microbiol. 10:1690, 2019.*
Abscess Information | Mount Sinai—New York, Abscess, accessed on Apr. 17, 2024.*
Dong Gun Lee et al., "Functional and structural characteristics of anticancer peptide Pep27 analogues", Cancer Cell International, vol. 5, Paper No. 21. 2005.
Notice of Allowance issued on Aug. 30, 2023 from Korean Patent Office in a counterpart Korean Patent Application No. 10-2021-0014180 (English translation is also submitted herewith.).

* cited by examiner

*Primary Examiner* — James H Alstrum-Acevedo
*Assistant Examiner* — Erinne R Dabkowski
(74) *Attorney, Agent, or Firm* — The PL Law Group, PLLC

(57) ABSTRACT

In a method of killing or reducing a growth of methicillin-resistant *Staphylococcus aureus* (*S. aureus*), a composition including a peptide consisting of the amino acid sequence of SEQ ID NO:2 or 3 is administered to a subject in need thereof. The peptide can be usefully applied as an active ingredient for antibiotics, cosmetic compositions, food additives, feed additives, biological pesticides and quasi-drugs.

4 Claims, 21 Drawing Sheets

Specification includes a Sequence Listing.

FIG. 18A

PEP27-2 (µM)

| Ceftriaxone (µM) | 0 | 1 | 2 | 4 |
|---|---|---|---|---|
| 0 | 1.00 | 0.61 | 0.27 | 0.05 |
| 4 | 0.68 | 0.35 | 0.19 | 0.04 |
| 8 | 0.57 | 0.05 | 0.04 | 0.04 |
| 16 | 0.34 | 0.04 | 0.05 | 0.03 |
| 32 | 0.05 | 0.04 | 0.03 | 0.04 |

| Ceftazidine (µM) | 0 | 1 | 2 | 4 |
|---|---|---|---|---|
| 0 | 1.00 | 0.61 | 0.27 | 0.05 |
| 4 | 0.72 | 0.43 | 0.16 | 0.04 |
| 8 | 0.52 | 0.28 | 0.09 | 0.04 |
| 16 | 0.40 | 0.04 | 0.05 | 0.03 |
| 32 | 0.05 | 0.04 | 0.03 | 0.04 |

| Meropenem (µM) | 0 | 1 | 2 | 4 |
|---|---|---|---|---|
| 0 | 1.00 | 0.61 | 0.27 | 0.05 |
| 0.5 | 0.49 | 0.03 | 0.05 | 0.04 |
| 1 | 0.18 | 0.04 | 0.05 | 0.03 |
| 2 | 0.05 | 0.04 | 0.03 | 0.04 |

Killing — *S. aureus* MW2 — Growth

SEQUENCE LISTING

```
Sequence total quantity: 5
SEQ ID NO: 1           moltype = AA  length = 27
FEATURE                Location/Qualifiers
REGION                 1..27
                       note = PEP27
```

```
MOD_RES                 27
                        note = AMIDATION
source                  1..27
                        mol_type = protein
                        organism = synthetic construct
SEQUENCE: 1
MRKEFHNVLS SGQLLADKRP ARDYNRK                                    27

SEQ ID NO: 2            moltype = AA  length = 27
FEATURE                 Location/Qualifiers
REGION                  1..27
                        note = PEP27-1
MOD_RES                 27
                        note = AMIDATION
source                  1..27
                        mol_type = protein
                        organism = synthetic construct
SEQUENCE: 2
MWKWFHNVLS SGQLLADKRP ARDYNRK                                    27

SEQ ID NO: 3            moltype = AA  length = 27
FEATURE                 Location/Qualifiers
REGION                  1..27
                        note = PEP27-2
MOD_RES                 27
                        note = AMIDATION
source                  1..27
                        mol_type = protein
                        organism = synthetic construct
SEQUENCE: 3
MWKWFHNVLS WGWLLADKRP ARDYNRK                                    27

SEQ ID NO: 4            moltype = AA  length = 27
FEATURE                 Location/Qualifiers
REGION                  1..27
                        note = PEP27-5
MOD_RES                 27
                        note = AMIDATION
source                  1..27
                        mol_type = protein
                        organism = synthetic construct
SEQUENCE: 4
MWKWFHNVLS SGQLLADKWW AWWYNWW                                    27

SEQ ID NO: 5            moltype = AA  length = 12
FEATURE                 Location/Qualifiers
REGION                  1..12
                        note = TAT
source                  1..12
                        mol_type = protein
                        organism = synthetic construct
SEQUENCE: 5
GRKKRRQRRR PQ                                                    12
```

PEPTIDE DERIVED FROM PEP27 PEPTIDE AND USES THEREOF

CROSS-REFERENCE TO RELATED APPLICATION AND CLAIM OF PRIORITY

This application is a divisional application of U.S. application Ser. No. 17/588,736, filed on Jan. 31, 2022, which claims priority to the benefit of Korean Patent Application No. 10-2021-0014180 filed in the Korean Intellectual Property Office on Feb. 1, 2021, the entire contents of which are incorporated herein by reference.

BACKGROUND

1. Field of the Invention

The present invention relates to a novel peptide derived from PEP27 peptide and uses thereof.

2. Description of the Related Art

Bacterial infections are one of the most common and fatal causes of human disease. Unfortunately, the abuse of antibiotics has resulted in antibiotic resistance of bacteria. Indeed, a rate at which bacteria become resistant to new antibiotics is much faster than a rate at which analogs of new antibiotics are developed. For example, bacterial species such as *Enterococcus faecalis, Mycobacterium tuberculosis* and *Pseudomonas aeruginosa*, which possibly threaten human life, have developed resistance to all antibiotics known to date.

Antibiotic tolerance is a distinctive phenomenon from antibiotic resistance, was firstly discovered in *Pneumococcus* sp. in the 1970s, and has provided significant clues to the mechanism of action of penicillin. Species showing tolerance to antibiotics stop growing but do not die in the presence of antibiotics at usual concentrations. Tolerance occurs because, when antibiotics inhibit cell wall synthetase, bacterial autolytic enzymes such as autolysin do not activate. Due to this fact, bacteria may be killed by penicillin that activates endogenous hydrolytic enzymes. On the other hand, the bacteria may inhibit the activity of the above enzymes, resulting in survival even during antibiotic therapy. It is clinically highly significant that bacteria have tolerance to diverse antibiotics. The reason is that, if it is impossible to eradicate tolerant bacteria, antibiotic treatment would be less effective in clinical infections. Further, developing tolerance is considered to be a pre-requisite for occurrence of resistance to antibiotics because of survival of strains despite the antibiotic therapy. Such strains acquire new genetic elements that are resistant to antibiotics and continue to grow even in the presence of antibiotics. Indeed, all bacteria resistant to antibiotics are known to have tolerance too, therefore, development for new antibiotics capable of killing the antibiotic-resistant bacteria is required. In aspect of activity mechanism, the antibiotic tolerance may be classified into two type pathways: first, a phenotypic tolerance, which occurs when a growth rate is reduced in all bacteria; and second, a genetic tolerance caused by mutation occurring in specific bacteria. In both cases, a primary phenomenon is occurrence of down regulation of autolysin activity, wherein the down regulation may be transient when it is phenotypically tolerant to external stimulation. On the other hand, the genetic tolerance with the resulting mutation, which causes a change in pathway to regulate cellular hemolysis, may be permanent. The simplest case of the genetic tolerance is occurrence of defects in the autolysin enzyme. For various uncertain reasons, strains having tolerance due to defects of apoptotic enzymes described above have not been clinically found. On the other hand, clinical tolerance is exhibited by regulating activity of autolysin. In order to cope with bacteria that are resistant to antibiotics, development of new antibiotics is required, and further development of new antibiotics acting independently of autolysin may also be required.

Meanwhile, bacteriocin is a natural antimicrobial protein generated by different types of microorganisms and has bactericidal activity to bacterial species similar to productive bacteria. The bacteriocin may be classified into three classes in terms of structure. The first is lantibiotics, the second is nonlantibiotics, and the third is proteins secreted by signal peptides. Animals including insects also produce naturally occurring peptide antibiotics. Also, the peptide antibiotics may be divided into three groups in terms of structure. The first is a cysteine-rich β-sheet peptide, the second is an α-helical amphiphilic molecule, and the third is a proline-rich peptide. These antimicrobial peptides are known to play an important role in host defense and the innate immune system. Specifically, these antimicrobial peptides have different structures depending on the amino acid sequence.

SUMMARY

An aspect of the present invention is to provide novel peptide and uses thereof.

To achieve the above aspect, the following technical solutions are adopted in the present invention.

1. A peptide in which, in the amino acid sequence of SEQ ID NO: 1, (i) $2^{nd}$ and $4^{th}$ amino acids are each substituted with tryptophan (W); (ii) $2^{nd}$, $4^{th}$, $11^{st}$ and $13^{rd}$ amino acids are each substituted with tryptophan; or (iii) $2^{nd}$, $4^{th}$, $19^{th}$, $20^{th}$, $22^{nd}$, $23^{rd}$, $26^{th}$ and $27^{th}$ amino acids are each substituted with tryptophan.

2. The peptide according to the above 1, wherein the peptide consists of the amino acid sequence of SEQ ID NO: 3.

3. The peptide according to the above 1, wherein the peptide has antimicrobial activity against at least one selected from the group consisting of gram-positive bacteria, gram-negative bacteria and antibiotics-tolerant bacteria.

4. The peptide according to the above 3, wherein the gram-positive bacteria are at least one selected from the group consisting of *Staphylococcus aureus, Bacillus subtilis* and *Listeria monocytogenes*.

5. The peptide according to the above 3, wherein the gram-negative bacteria are at least one selected from the group consisting of *Escherichia coli, Pseudomonas aeruginosa* and *Salmonella typhimurium*.

6. The peptide according to the above 3, wherein the antibiotics-tolerant bacteria are at least one selected from the group consisting of *Staphylococcus aureus* (*S. aureus*), *Escherichia coli* (*E. coli*), *Pseudomonas aeruginosa* (*P. aeruginosa*) and *Salmonella typhimurium* (*S. typhimurium*), which have antibiotic tolerance.

7. An antimicrobial composition including the peptide according to any one of the above 1 to 6 as an active ingredient.

8. The antimicrobial composition according to the above 7, wherein the antimicrobial composition is a pharmaceutical composition.

9. The antimicrobial composition according to the above 7, wherein the antimicrobial composition is any one selected from the group consisting of cosmetic compositions, food additives, feed additives, biological pesticides, antiseptic compositions and quasi-drug compositions.

The peptide of the present invention has excellent antimicrobial activity and low cytotoxicity, whereby it can be usefully used as an active ingredient of antibiotics, cosmetic compositions, food additives, feed additives, biological pesticides, quasi-drugs and the like.

BRIEF DESCRIPTION OF THE DRAWINGS

The above and other objects, features and other advantages of the present invention will be more clearly understood from the following detailed description taken in conjunction with the accompanying drawings, in which:

FIGS. 1A to 1C illustrate results of confirming the secondary structure of each of the antimicrobial PEP27 peptide (control) and a new peptide, that is, PEP27-2 as a PEP27 analog in which an amino acid residue is substituted (experimental group), respectively, in a membrane-like environment, wherein FIG. 1A shows an aqueous solution (10 mM PBS solution), FIG. 1B shows a bacterial membrane-mimic artificial membrane composed of PE/PG(7/3), and FIG. 1C shows an eukaryotic cell-mimic artificial membrane composed of PC/CH/SM (1/1/1);

FIG. 15A illustrates inner membrane permeability. Hydrolysis of ONPG (n=3 per condition) due to the release of cytoplasmic β-galactosidase in *E. coli* ATCC 25922 cells treated with the indicated peptides at 1×MIC was measured for 60 min at 420 nm. ***$P<0.001$ vs PEP27. FIG. 15B to FIG. 15E illustrate the changes in cytoplasmic membrane potential indicated by the membrane potential-sensitive dye DiSC$_3$-5 (n=4 per condition) in *E. coli* ATCC 25922 cells treated with PEP27 (FIG. 15B), PEP27-2 (FIG. 15C), buforin 2 (FIG. 15D), or melittin (FIG. 15E).

FIG. 17A illustrates Fluorescence microscopy analysis of biofilms formed by MDR bacteria after treatment with PEP27-2 at 1×MBIC. Live cells were stained with SYTO9. FIG. 17B and FIG. 17C illustrate the effect of PEP27-2 on biofilm formation by standard bacteria (FIG. 17B) and MDR bacteria (FIG. 17C).

FIGS. 18A to 18C illustrate the synergistic action of PEP27-2. FIG. 18A and FIG. 18B illustrate that the synergistic action of PEP27-2 and antibiotics killed *S. aureus* MW2. Logarithmically grown (5×10$^5$) *S. aureus* MW2 was incubated with indicated combinations of PEP27-2 and antibiotics in PBS containing 0.5% TSB at 37° C. shaking. After 3 h of incubation, several dilutions of the bacterial suspensions were plated onto TSB agar plates. The next day *S. aureus* MW2 CFUs were counted. Each experiment was performed in triplicate. The data represent the average of three independent experiments±SD: *$P<0.05$, $P<0.01$, *$P<0.001$ vs untreated control. Data were analyzed by one-way ANOVA. FIG. 18C illustrates the combination index of PEP27-2 and antibiotics. Combination index was calculated using CompuSyn (ComboSyn Inc.) and indicated in medium effect plots as a function of the bacteria antagonistic effects as a function of the bacteria fractions affected by the combinatorial antibiotic treatment. Combination index value of 1 indicated additive effects, whereas values <1 and >1 indicated synergistic and antagonistic effects, respectively.

DETAILED DESCRIPTION

Figures 1A, 1B, 1C:
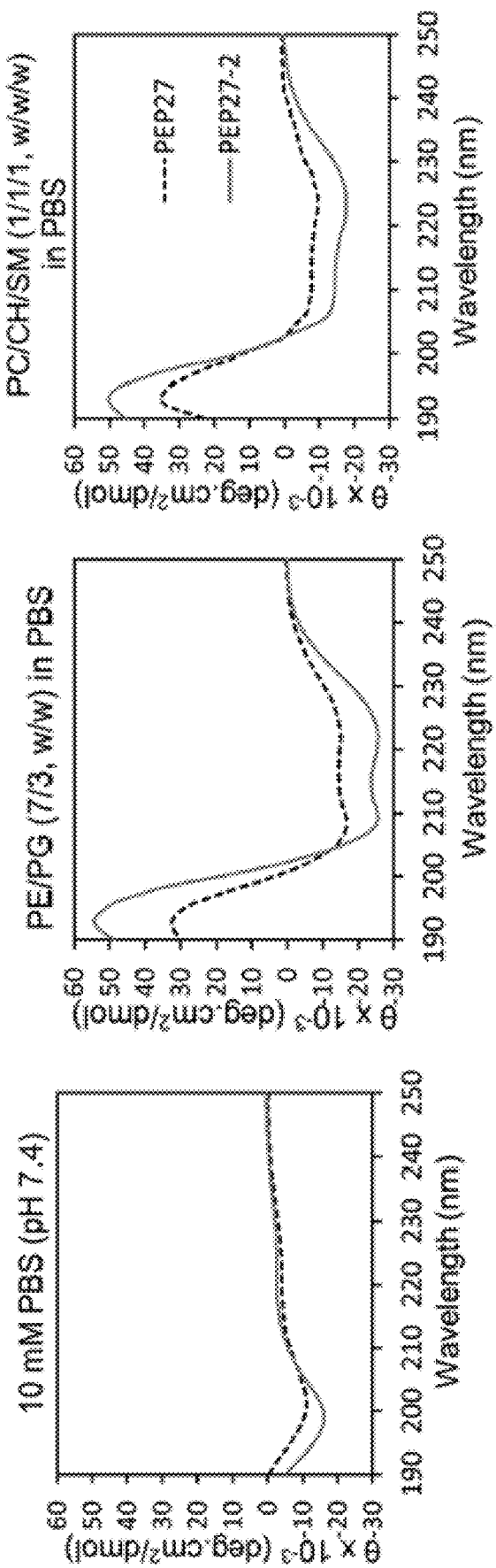

Hereinafter, the present invention will be described in detail.

The present invention provides a peptide in which, in the amino acid sequence of SEQ ID NO: 1, (i) $2^{nd}$ and $4^{th}$ amino acids are each substituted with tryptophan (W); (ii) $2^{nd}$, $4^{th}$, $11^{st}$ and $13^{rd}$ amino acids are each substituted with tryptophan; or (iii) $2^{nd}$, $4^{th}$, $19^{th}$, $20^{th}$, $22^{nd}$, $23^{rd}$, $26^{th}$ and $27^{th}$ amino acids are each substituted with tryptophan.

PEP27, a parental peptide consisting of the amino acid sequence of SEQ ID NO: 1, is secreted from Streptococcus pneumoniae, and is known as a "death signal peptide" existing at Vex123-Pep27-VncRS gene site.

(SEQ ID NO: 1)
MRKEFHNVLSSGQLLADKRPARDYNRK-NH$_2$

PEP27 peptide is possibly prepared by any conventional peptide synthesis method known in the art, and the preparation method thereof is not particularly limited. For example, the method for synthesis of PEP27 peptide used herein may include the typical chemical synthesis method of peptide in the art, specifically, the solution-phase peptide synthesis method, the solid-phase peptide synthesis method, the fragment condensation method, and the F-moc or T-BOC chemical method.

The peptide of the present invention may be peptides consisting of any one amino acid sequence selected from the group consisting of SEQ ID NOS: 2 to 4.

(SEQ ID NO: 2)
MWKWFHNVLSSGQLLADKRPARDYNRK-NH$_2$ (SEQ ID NO: 3)
MWKWFHNVLSWGWLLADKRPARDYNRK-NH$_2$ (SEQ ID NO: 4)
MWKWFHNVLSSGQLLADKWWAWWYNWW-NH$_2$

The peptide consisting of the amino acid sequence of SEQ ID NO: 2 is a peptide, in which $2^{nd}$ and $4^{th}$ amino acids in PEP27 as the parental peptide are each substituted with tryptophan (W), and refers to as PEP27-1.

The peptide consisting of the amino acid sequence of SEQ ID NO: 3 is a peptide, in which $2^{nd}$, $4^{th}$, $11^{st}$ and $13^{rd}$ amino acids in PEP27 as the parental peptide are each substituted with tryptophan (W), and refers to as PEP27-2.

The peptide consisting of the amino acid sequence of SEQ ID NO: 4 is a peptide, in which $2^{nd}$, $4^{th}$, $19^{th}$, $20^{th}$, $22^{nd}$, $23^{rd}$, $26^{th}$ and $27^{th}$ amino acids in PEP27 as the parental peptide are each substituted with tryptophan (W), and refers to as PEP27-5.

"—NH$_2$" in each of the amino acid sequences of SEQ ID NOS: 1 to 4 indicates that a carboxyl group at C terminal was changed by amidation.

Specifically, the peptide of the present invention may be a peptide consisting of the amino acid sequence of SEQ ID NO: 3.

The amino acid substitution as described above may induce increase/decrease of electrode and reduce cytotoxicity of the peptide. Further, the peptide may represent antimicrobial activity against gram-positive bacteria, gram-negative bacteria and antibiotics-tolerant bacteria by the amino acid substitution described above.

The peptide of the present invention may exhibit antimicrobial activity against gram-positive bacteria, gram-negative bacteria and antibiotics-tolerant bacteria.

The gram-positive bacteria may be at least one selected from the group consisting of Staphylococcus, Listeria, Corynebacterium, Lactobacillus and Bacillus, but they are not limited thereto. Specifically, the peptide of the present may represent excellent antimicrobial activity against at least one selected from Staphylococcus, Bacillus or Listeria.

The gram-negative bacteria may be at least one selected from the group consisting of Pseudomonas, Escherichia, Salmonella, Leptospira and Rickettsia, but they are not limited thereto. Specifically, the peptide of the present invention may exhibit excellent antimicrobial activity to at least one selected from the group consisting of Pseudomonas, Escherichia or Salmonella.

The antibiotics-tolerant bacteria may be at least one selected from the group consisting of Pseudomonas aeruginosa, Escherichia coli, Salmonella typhimurium and Staphylococcus aureus, which have antibiotic tolerance, but they are not limited thereto. The antibiotics described above may include at least one selected from the group consisting of aminoglycoside series (aminoglycoside, gentamicin, neomycin, etc.), penicillin series (ampicillin, etc.), sulfonamide series, beta-lactam series (beta-lactam, amoxicillin/clavulanic acid), chloramphenicol series, erythromycin series, fluorphenicol series, phosphomycin series, kanamycin series, lincomycin series, methicillin series, quinolone series, streptomycin series, tetracycline series, trimethoprim series and vancomycin series of antibiotics, but they are not limited thereto.

The peptide of the present invention may represent low cytotoxicity within antimicrobial concentration in regard to human-derived cells while having excellent antimicrobial activity to the gram-positive bacteria, gram-negative bacteria and antibiotics-tolerant bacteria.

Further, the present invention provides an antimicrobial composition including the peptide described above as an active ingredient.

The antimicrobial composition may be a pharmaceutical composition. That is, the present invention provides a pharmaceutical composition for antimicrobial use, which includes the peptide described above as an active ingredient.

Peptide analogs derived from PEP27 antimicrobial peptide of the present invention, that is, amino acid sequences of SEQ ID NOS: 2 to 4 may show strong antimicrobial activity and have low cytotoxicity to human-derived cells, whereby the peptide of the present invention can be usefully used as an active ingredient of an antimicrobial pharmaceutical composition. For example, the peptide of the present invention may be used as one of antibiotics. For example, the peptide of the present invention may be used in combination with other antibiotics and, when used in combination with other antibiotics, may represent synergistic antimicrobial activity compared to using the same alone.

The pharmaceutical composition may further include any appropriate carrier, excipient and diluents, which are commonly used in manufacturing a pharmaceutical composition, in addition to the peptide described above as an active ingredient.

The carrier, excipient and diluents possibly included in the pharmaceutical composition may include, for example, lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil.

The pharmaceutical composition may be administered orally or parenterally during clinical administration, and may be used in the form of any typical pharmaceutical formulation. Parenteral administration may refer to administration through a route other than oral administration, such as rectal, intravenous, peritoneal, muscle, arterial, transdermal, nasal, inhalation, ocular and subcutaneous administration.

The pharmaceutical composition may further contain one or more active ingredients exhibiting the same or similar functions as the peptide which is the active ingredient described above.

For example, the pharmaceutical composition of the present invention may further include any antibiotics known in the art.

The known antibiotics may be at least one selected from the group consisting of aminoglycoside series (aminoglycoside, gentamicin, neomycin, etc.), penicillin series (ampicillin, etc.), sulfonamide series, beta-lactam series (beta-lactam, amoxicillin/clavulanic acid), chloramphenicol series, erythromycin series, fluorphenicol series, phosphomycin series, kanamycin series, lincomycin series, methicillin series, quinolone series, streptomycin series, tetracycline series, trimethoprim series and vancomycin series of antibiotics. Specifically, the antibiotics may be at least one selected from the group consisting of meropenem, ceftazidime, ceftriaxone, doripenem, ertapenem, imipenem, cilastatin, cefadroxil, cefazolin, cephalexin, cefaclor, cefotetan, cefoxitin, cefprozil, cefuroxime, cefdinir, cefditoren, cefixime, cefotaxime, cefpodoxime, ceftibuten, cefepime and ceftaroline. More specifically, the antibiotics may be at least one selected from the group consisting of meropenem, ceftazidime and ceftriaxone.

An effective dose of the peptide of the present invention may range from 0.1 to 2 mg/kg, and the peptide may be administered once to 3 times a day.

With regard to the peptide of the present invention, a total effective amount of the peptide may be administered to a patient in the form of a bolus or in a single dose by infusion or the like for a relatively short period of time. Alternatively, the peptide may be administered according to fractionated treatment protocol in which multiple doses are administered over a long period of time. With regard to a concentration of the peptide described above, considering that an effective dosage to a patient is determined by taking into account different factors such as the patient's age and health condition, as well as administration routes and the number of treatments of a drug, the effective dosage of the peptide of the present invention may be appropriately determined for specific uses of the peptide as an antibiotic by those skilled in the art.

The antimicrobial composition may be any one selected from the group consisting of a cosmetic composition, food additives, feed additives, biological pesticides, an antiseptic composition and a quasi-drug composition.

The present invention provides an antimicrobial cosmetic composition which includes the peptide described above as an active ingredient.

The amino acid sequences of SEQ ID NOS: 2 to 4 as peptide analogs derived from PEP27 antimicrobial peptide according to the present invention may show strong antimicrobial activity and have low cytotoxicity to human-derived cells, whereby the peptide of the present invention can be usefully used as an active ingredient of an antimicrobial cosmetic composition.

The cosmetic composition may further include components generally used in a cosmetic composition, in addition to the peptide described above as an active ingredient. For example, the cosmetic composition may include at least one among conventional auxiliary agents such as antioxidants, stabilizers, solubilizers, vitamins, pigments and fragrances, and carriers.

The cosmetic composition may include the peptide as an active ingredient in an amount of 0.1 to 50% by weight ("wt. %"), and preferably 1 to 10 wt. %.

The cosmetic composition may be prepared in any type of formulations commonly manufactured in the art, for example, may be formulated in the form of solution, suspension, emulsion, paste, gel, cream, lotion, powder, soap, surfactant-containing cleansing, oil, powder foundation, emulsion foundation, wax foundation, spray, etc., but it is not limited thereto.

If the formulation of the cosmetic composition is a paste, cream or gel, animal oil, vegetable oil, wax, paraffin, starch, tragacanth, cellulose derivatives, polyethylene glycol, silicone, bentonite, silica, talc, or zinc oxide may be used as a carrier component.

If the formulation of the cosmetic composition is a powder or spray, lactose, talc, silica, aluminum hydroxide, calcium silicate or polyamide powder may be used as a carrier component. In particular, for a spray formulation, a propellant such as chlorofluorohydrocarbon, propane/butane or dimethylether may be further included.

If the formulation of the cosmetic composition is a solution or emulsion, a solvent, solubilizer or emulsifier may be used as a carrier component. For example, water, ethanol, isopropanol, ethyl carbonate, ethyl acetate, benzyl alcohol, benzyl benzoate, propyleneglycol, 1,3-butylglycol oil, glycerol aliphatic ester, polyethylene glycol or fatty acid ester of sorbitan may be used.

If the formulation of the cosmetic composition is a suspension, a liquid diluent such as water, ethanol or propyleneglycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, or the like may be used as a carrier component.

If the formulation of the cosmetic composition is a surfactant-containing cleansing agent, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, fatty alcohols, fatty acid glycerides, fatty acid diethanolamides, vegetable oils, lanolin derivatives or ethoxylated glycerol fatty acid esters may be used as a carrier component.

The present invention provides an antimicrobial food additive which includes the peptide described above as an active ingredient.

The amino acid sequences of SEQ ID NOS: 2 to 4 as peptide analogs derived from PEP27 antimicrobial peptide of the present invention may show strong antimicrobial activity and have low cytotoxicity to human-derived cells, whereby the peptide of the present invention can be usefully used as an active ingredient of an antimicrobial food additive.

When the peptide of the present invention is used as a food additive, the peptide may be added at it is or may be used together with other food ingredients. A mixing amount of the active ingredient may be appropriately determined depending on the purpose of use. For example, the peptide of the present invention may be added in an amount of 15 parts by weight ("wt.parts") or less, and preferably 10 wt.parts or less based on the raw material. However, in the case of long-term intake, the above amount may be the above range or less, and since there is no problem in terms of stability, the active ingredient may be used even in an amount of the above range or more.

The food to which the peptide of the present invention is able to be added may include, for example, meat, sausage, bread, chocolate, candies, snacks, confectionery, pizza, ramen, other noodles, gums, dairy products including ice cream, various soups, beverages, tea, drinks, alcoholic beverages and vitamin complexes, and all foods in the usual sense are included.

The present invention provides an antimicrobial feed additive which includes the peptide described above as an active ingredient.

The amino acid sequences of SEQ ID NOS: 2 to 4 as peptide analogs derived from PEP27 antimicrobial peptide of the present invention may show strong antimicrobial activity and have low cytotoxicity to human-derived cells, whereby the peptide of the present invention can be usefully used as an active ingredient of an antimicrobial feed additive.

When the peptide of the present invention is used as the feed additive, effects of replacing existing antibiotics, suppressing the growth of harmful food pathogens thus to enhance the health condition of the animal body, improving the weight gain and meat quality of livestock, and increasing milk production and immunity may be acquired. When the peptide of the present invention is used as a feed additive, the feed may be prepared in the form of fermented feed, blended feed, pellet form, and silage.

The fermented feed may be produced by adding a variety of microorganism groups or enzymes as well as the peptide of the present invention to the feed and then fermenting organic substances therein, while the blended feed may be produced by admixing various types of general feeds as well as the peptide of the present invention. Further, the pellet-type feed may be produced by applying heat and pressure to the blended feed in a pellet machine, while the silage may be produced by fermenting fresh-cut forage with microorganisms. In addition, wet fermented feed may be produced by collecting and transporting organic materials such as food waste, sterilizing the same, blending the same with excipients for adjusting water content at a predetermined ratio, followed by fermenting the mixture at a temperature suitable for fermentation for 24 hours or more and adjusting the water content to reach about 70%. Fermented dry feed may be produced by adjusting the water content through a drying process to reach 30 to 40%.

The present invention also provides an antimicrobial antiseptic composition, an antimicrobial biological pesticide and an antimicrobial quasi-drug, each of which includes the peptide of the present invention as an active ingredient.

The amino acid sequences of SEQ ID NOS: 2 to 4 as peptide analogs derived from PEP27 antimicrobial peptide of the present invention may show strong antimicrobial activity and have low cytotoxicity to human-derived cells, whereby the peptide of the present invention can be usefully used as an active ingredient of an antimicrobial antiseptic composition, an antimicrobial biological pesticide and an antimicrobial quasi-drug, respectively.

The antimicrobial antiseptic composition may include, for example, food preservatives, cosmetic preservatives and pharmaceutical preservatives. The food preservatives, cosmetic preservatives and pharmaceutical preservatives are additives used to prevent deterioration, spoilage, discoloration and chemical modification. For example, fungicides and antioxidants may be included, and functional antibiotics for suppressing the growth of microorganisms such as bacteria, mold, yeast, etc. thus to inhibit the growth of spoilage microorganisms or sterilize the same in food and medicines may be further included. Desirable conditions for such antiseptic composition as described above may include non-toxicity and effectiveness even with trace amounts.

When the composition of the present invention is used as a quasi-drug composition, the peptide as an active ingredient may be added at it is or used together with other quasi-drugs or quasi-drug components.

The quasi-drug composition may include, for example, disinfectant cleaner, shower foam, mouthwash, wet tissue, a detergent soap, hand wash, humidifier filler, mask, ointment, patch or filter filler.

Further, the present invention provides an antimicrobial treatment method which includes administering a pharmaceutically effective amount of the antimicrobial peptide to a subject.

The subject may be a mammal other than a human, but it is not limited thereto.

Hereinafter, the present invention will be concretely described by means of the following examples. However, these examples are only illustrative of the present invention, and the scope and range of the present invention are duly not limited thereto.

EXAMPLE

1. Synthesis and Purification of Peptides

According to the method of synthesizing a liquid peptide (Merrifield, R B., J. Am. Chem. Soc., 85, 2149, 196) of Merrifield, a peptide was synthesized (SEQ ID NO: 2) by substituting $2^{nd}$ and $4^{th}$ amino acid residues, which are present in the amino acid sequence of PEP27 as the parental peptide defined with the amino acid sequence of SEQ ID NO: 1, with tryptophan (W). Further, another peptide was synthesized by substituting $11^{st}$, $13^{rd}$ or $19^{th}$, $20^{th}$, $22^{nd}$, $23^{rd}$, $26^{th}$ and $27^{th}$ amino acid residues, which are present in the amino acid sequence of SEQ ID NO: 2, with tryptophan (W) (Table 1).

Specifically, the peptide having a carboxyl terminal in the form of $NH_2$ designed in the present invention was obtained using a link amide MBHA-resin as a starting material, and the peptide having a carboxyl terminal in the form of OH was obtained using Fmoc (9-fluorenyl methoxycarbonyl)-amino acid-Wang resin as a starting material. Extension of peptide chains by Fmoc-amino acid coupling was implemented by DCC (N-hydroxy benzotriazole (HOBt)-dicyclohexycarbodiimide) method. After coupling the Fmoc-amino acid at the amino terminal of each peptide, Fmoc group was removed with NMP (20% piperidine/N-methyl pyrrolidone) solution, followed by washing several times with NMP and DCM (dichloromethane) and then drying the same with nitrogen gas. To the prepared peptide, a mixed solution of trifluoroacetic acid (TFA), phenol, thioanisole, $H_2O$ and triisopropylsilane at a ratio of 85:5:5:2.5:2.5 (v/v), respectively, was added, followed by reaction for 2 to 3 hours to remove the protective group and to separate the peptide from the resin. Thereafter, the peptide was obtained by precipitation with diethylether. The obtained crude peptide was purified in reverse phase (RP)-HPLC column (Delta Pak, C18300 Å, 15, 19.0 mm×30 cm, Waters, USA) in an acetonitrile gradient containing 0.05% TFA. After hydrolyzing the synthetic peptide at 110° C. with 6N hydrochloric acid, the residue was concentrated under reduced pressure and dissolved in 0.02N hydrochloric acid, followed by measuring the constitutional composition of amino acid using an amino acid analyzer (Hitachi 8500 A). Then, in order to determine purity and a molecular weight of the peptide, MALDI mass spectrometry (Hill, et al., Rapid Commun. Mass Spectrometry, 5: 395, 1991) was performed.

As a result, as shown in Table 1 below, the peptides defined with the amino acid sequences of SEQ ID NOS: 1 to 4 were synthesized with the purity of 95% or more, and the molecular weights thereof were confirmed to be substantially the same as expected molecular weights.

TABLE 1

| Name of peptide | Amino acid sequence | SEQ ID NO. | Molecular weight |
|---|---|---|---|
| PEP27 | MRKEFHNVLSSGQLLADKR PARDYNRK-NH$_2$ | 1 | 3228.7 |
| PEP27-1 | MWKWFHNVLSSGQLLADKR PARDYNRK-NH$_2$ | 2 | 3316.9 |
| PEP27-2 | MWKWFHNVLSWGWLLADKR PARDYNRK-NH$_2$ | 3 | 3474.1 |
| PEP27-5 | MWKWFHNVLSSGQLLADKW WAWWYNWW-NH$_2$ | 4 | 3625.2 |

With reference to the sequence of PEP27 (SEQ ID NO: 1), types of substituted amino acids of novel peptides (SEQ ID NOS: 2 to 4) and substitution sites thereof are shown in Table 2 below.

TABLE 2

| Number of amino acid | PEP27 | PEP27-1 | PEP27-2 | PEP27-5 |
|---|---|---|---|---|
| 1 | M | | | |
| 2 | R | W | W | W |
| 3 | K | | | |
| 4 | E | W | W | W |
| 5 | F | | | |
| 6 | H | | | |
| 7 | N | | | |
| 8 | V | | | |
| 9 | L | | | |
| 10 | S | | | |
| 11 | S | | W | |
| 12 | G | | | |
| 13 | Q | | W | |
| 14 | L | | | |
| 15 | L | | | |
| 16 | A | | | |
| 17 | D | | | |
| 18 | K | | | |
| 19 | R | | | W |
| 20 | P | | | W |
| 21 | A | | | |
| 22 | R | | | W |
| 23 | D | | | W |
| 24 | Y | | | |
| 25 | N | | | |
| 26 | R | | | W |
| 27 | K | | | W |

(Blank: no substitution of amino acid)

2. Measurement of Antimicrobial Activity

In order to evaluate the antimicrobial activity of the peptides prepared by the method of above 1, a minimal inhibitory concentration (MIC) value as the minimum concentration of a peptide, in which cells are not divided, was measured.

Specifically, the strains shown in Table 3 below were purchased, cultured in a medium having a constitutional composition suitable for each strain to a mid-log phase, and then diluted to a concentration of $2 \times 10^4$ cells/100 µl to prepare the product on a micro-titration plate (Nunc, USA). Then, PEP27, PEP27-1, PEP27-2 or PEP27-5 peptide synthesized in the above 1 was added to each well by serial dilution ½ times, followed by incubation at 37° C. for 18 hours. Thereafter, using a micro-titration plate reader (Merck Elisa reader, Germany), absorbance was measured at a wavelength of 600 nm to determine the MIC value for each strain. PEP27 as the parental peptide was used as a control, while buformin 2 and melittin were used as comparison peptides.

TABLE 3

| Name of strain | Division | Origin | Deposit No. |
|---|---|---|---|
| Staphylococcus aureus | Gram-positive bacteria | American Type Culture Collection (ATCC) | ATCC25923 |
| | | ATCC | ATCC29213 |
| | Antibiotics-tolerant gram-positive bacteria | Isolated cell line USA 300 | |
| | | Isolated cell line MW2 (USA 400) | |
| | | Culture Collection of Antimicrobial Resistant Microbes (CCARM) | CCARM3089 |
| | | CCARM | CCARM3090 |
| | | CCARM | CCARM3518 |
| | | Transformed strain MW2-GFP | |
| Pseudomonas aeruginosa | Gram-negative bacteria | ATCC | ATCC15692 |
| | | ATCC | ATCC27853 |
| | Antibiotics-tolerant gram-negative bacteria | Isolated cell line 4007 | |
| | | Isolated cell line 4891 | |
| Escherichia coli | Gram-negative bacteria | ATCC | ATCC25922 |
| | | ATCC | ATCC27853 |
| | Antibiotics-tolerant gram negative bacteria | CCARM | CCARM1229 |
| | | CCARM | CCARM1238 |
| Salmonella typhimurium | Gram-negative bacteria | Korean Culture Type Collection (KCTC) | KCTC1926 |
| | Antibiotics-tolerant gram-negative bacteria | CCARM | CCARM8007 |
| | | CCARM | CCARM8008 |
| Bacillus subtilis | Gram-positive bacteria | KCTC | KCTC1998 |
| Listeria monocytogenes | Gram-positive bacteria | KCTC | KCTC3710 |

As a result, as shown in Table 4 below, it was confirmed that PEP27-2 peptide showed noticeably excellent antimicrobial activity to gram-positive bacteria, gram-negative bacteria and antibiotics-tolerant bacteria, as compared to the control, that is, the parental PEP27 peptide and other novel peptides.

TABLE 4

| Peptide Strain | Minimal inhibitory concentration (μM) | | | | | |
|---|---|---|---|---|---|---|
| | PEP27 | PEP27-1 | PEP27-2 | PEP27-5 | Buforin | Melittin |
| Gram-positive bacteria | | | | | | |
| S. aureus ATCC25923 | 32 | 32 | 2 | >64 | 16 | 2 |
| S. aureus ATCC29213 | 32 | 32 | 2 | >64 | 16 | 2 |
| B. subtilis KCTC1998 | 64 | 32 | 4 | >64 | 32 | 4 |
| L. monocytogens KCTC3710 | 32 | 64 | 8 | >64 | 64 | 4 |
| Gram-negative bacteria | | | | | | |
| E. coli ATCC25922 | 64 | 64 | 4 | >64 | 64 | 2 |
| E. coli ATCC27325 | 64 | 32 | 4 | >64 | 64 | 2 |
| P. aeruginosa ATCC15692 | 64 | 32 | 4 | >64 | 32 | 2 |
| P. aeruginosa ATCC27853 | 64 | 32 | 4 | >64 | 32 | 2 |
| Sa. typhimurium KCTC1926 | 64 | 32 | 8 | >64 | 32 | 4 |
| Antibiotics-tolerant gram-positive bacteria | | | | | | |
| S. aureus CCARM3089 | 32 | 32 | 4 | >64 | 32 | 2 |
| S. aureus CCARM3090 | 32 | 16 | 4 | >64 | 32 | 4 |
| S. aureus CCARM3518 | 32 | 32 | 4 | >64 | 32 | 2 |
| S. aureus USA300 | 32 | 32 | 2 | >64 | 32 | 2 |
| S. aureus MW2 | 32 | 32 | 3 | >64 | 64 | 4 |
| Antibiotics-tolerant gram-negative bacteria | | | | | | |
| E. coli CCARM1229 | 64 | 32 | 4 | >64 | 64 | 2 |
| E. coli CCARM1238 | 64 | 32 | 4 | >64 | 64 | 4 |
| P. aeruginosa 4007 | 64 | 32 | 4 | >64 | 32 | 2 |
| P. aeruginosa 4891 | 64 | 32 | 4 | >64 | 64 | 2 |
| Sa. typhimurium CCARM8007 | 64 | 32 | 4 | >64 | 32 | 4 |
| Sa. typhimurium CCARM8009 | 64 | 32 | 4 | >64 | 32 | 4 |

Figure 11B:
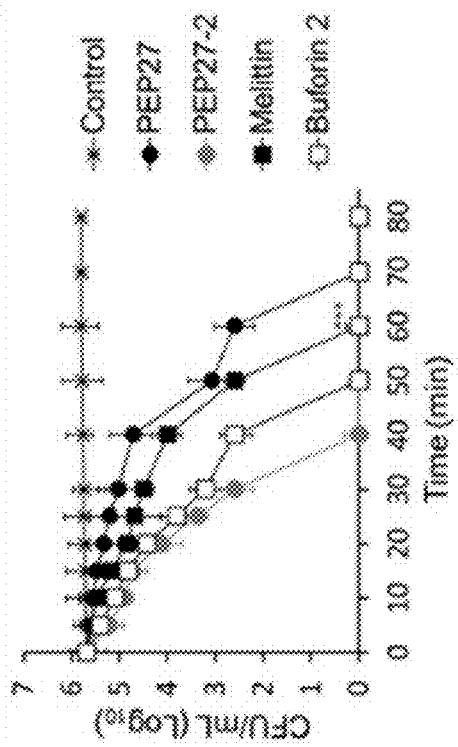
FIGS. 11A to FIG. 12 illustrate time kill kinetics of PEP27 and its analogs. *E. coli* ATCC 25922 (FIG. 11A) and *S. aureus* ATCC 25923 (FIG. 11B) were incubated with PEP27 or PEP27-2 at their MICs for 0-80 min. Symbols represent the mean±SD of pooled data from three independent experiments (***$P<0.001$). Total bacterial population was stained with the QUANTOM total cell staining dye (FIG. 12). The intracellular fluorescence was imaged using the QUANTOM Tx microbial cell counter, which captures and counts cells automatically. Data in FIGS. 11A and 11B were analyzed by one-way ANOVA.
Figure 11A:
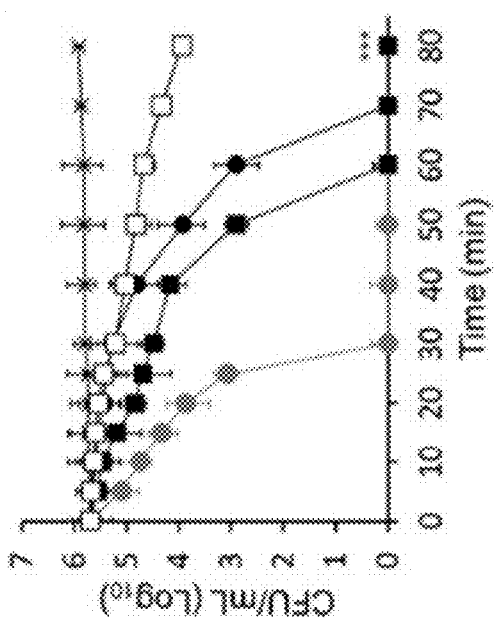
Figure 12:
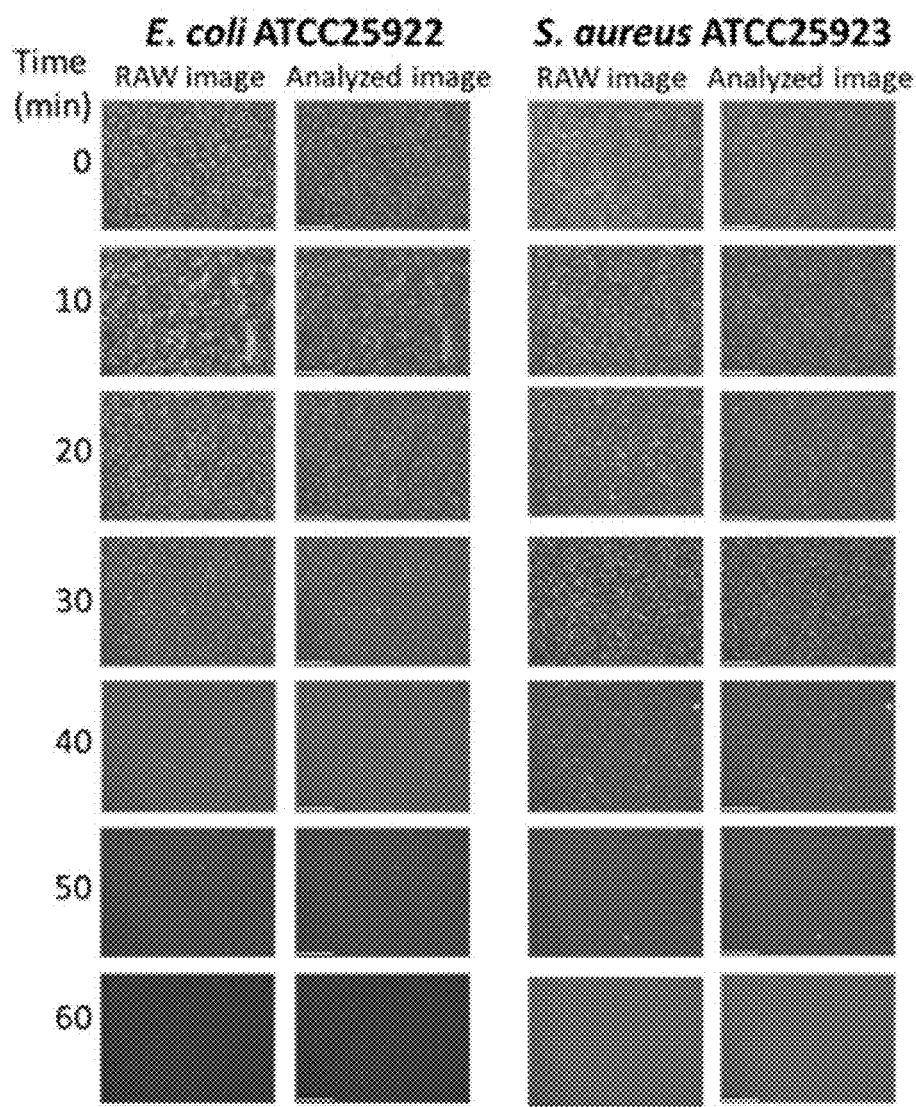

The results of time-kill analysis of PEP27 and PEP27-2 against *E. coli* ATCC 25922 and *S. aureus* ATCC 25923 are shown in FIGS. 11A to 12.

Time-killing kinetics were analyzed for *E. coli* ATCC 25922 and *S. aureus* ATCC 25923 in the presence of PEP27-2 at their respective MICs. The bacterial cells were cultured overnight until they reached the exponential growth phase; they were then incubated at 37° C. for an additional 10 min from 0 min to 1 h. The total bacterial population was then stained with QUANTOM total cell staining dye, after which the stained cells were mixed with QUANTOM cell loading buffer and loaded into QUANTOM M50 Slides. The slides were centrifuged using the QUANTOM centrifuge to evenly distribute them throughout the counting chamber and ensure accurate cell counts. Intracellular fluorescence was detected using the QUANTOM Tx microbial cell counter, which captures and counts cells automatically (Logos Biosystems, Gyeonggi-do, South Korea).

PEP27-2 induced a decrease in *E. coli* cell viability of $1.86 \times 10^9$ and in *S. aureus* of $1.60 \times 10^9$ (98.63% and 97.48%, respectively) after 20 min of treatment, with complete killing at 30 and 40 min, respectively (FIGS. 11A and 11B).

To monitor the changes in bacterial viability caused by the peptides, we monitored the fluorescence spectra of bacterial samples stained with QUANTOM total cell staining dye. The results showed that PEP27-2 killed both strains within 60 min in the time-kill kinetics (FIG. 12).

3. Measurement of Hemolytic Activity

In order to compare the cytotoxicity of the peptides prepared by the method of above 1, erythrocyte hemolytic activity of each of the synthesized peptides was measured.

Specifically, red blood cells of a rat (Balb/c, 6 weeks old, female) were diluted with PBS (pH 7.0) to a concentration of 8%, and PEP27, PEP27-1, PEP27-2 and PEP27-5 peptides were used for treatment of the cells at concentrations of 3.13, 6.25, 12.5, 25.01 50.0 and 100.0 μM/well, respectively, followed by reaction at 37° C. for 1 hour. Then, an amount of hemoglobin contained in the supernatant obtained by centrifugation at 1,000×g was determined by measuring the absorbance at a wavelength of 414 nm. As a control which is a standard for the degree of cell destruction, the absorbance of the obtained supernatant was measured after treatment using 1% Triton X-100 (Sigma, USA) and reaction at 37° C. for 1 hour. With reference to 100% erythrocytes hemolysis activity, hemolysis of each peptide was calculated from the measured absorbance using Equation 1 below.

Erythrocyte destruction ability (%)=(Absorbance A−Absorbance B)/(Absorbance C−Absorbance B)×100  [Equation 1]

(wherein, absorbance A represents the absorbance of a reaction solution treated with each peptide measured at a wavelength of 414 nm; absorbance B represents the absorbance of a reaction solution treated with PBS measured at a wavelength of 414 nm; and absorbance C represents the absorbance of a reaction solution treated with 1% Triton X-100 measured at a wavelength of 414 nm).

Figure 13:
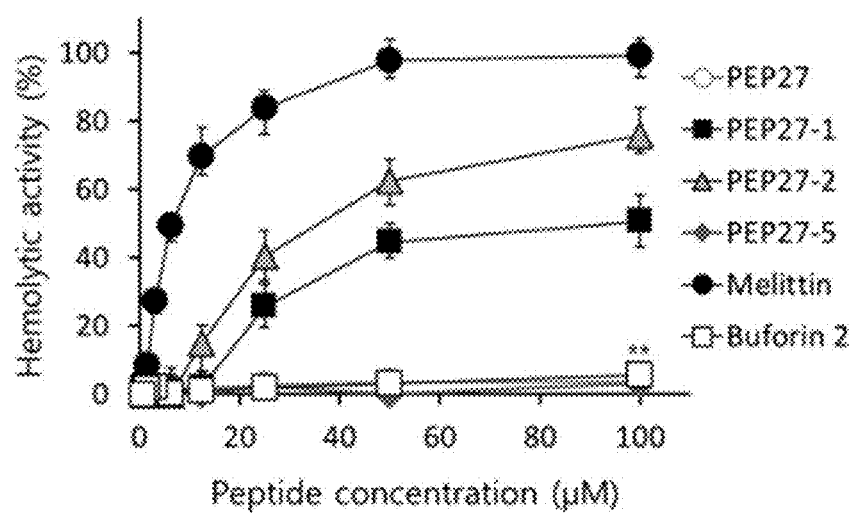
FIG. 13 illustrates the dose-response curve for hemolytic activity against mRBCs (n=3 per condition). Data in FIG. 13 were analyzed by one-way ANOVA. **$P<0.01$.

As a result, as shown in Table 5 below and FIG. 13, although PEP27 peptide as the parental peptide showed only 3.58% of hemolytic action to rat erythrocytes when treated at a concentration of 100 μM, it was confirmed that PEP27-2 peptide appeared occurrence of 75.8% hemolysis on erythrocytes even at the concentration of 100 μM, thereby increasing toxicity. However, toxicity was increased due to increase in activity, and it was confirmed that the toxicity is not found within the range of antimicrobial activity.

treatment with PEP27, PEP27-1, PEP27-2, and PEP27-5 were 100%, 41%-42%, 19%-23%, and 100%, respectively. Melittin strongly reduced the viability of all mammalian cells tested, with the lowest cell viability of 0.76%. PEP27-2 showed more potent antimicrobial activity than the parental peptide. PEP27-2 showed cytotoxic effects when high concentrations of the peptide were used to treat mouse erythrocytes and human cells. These results agree with those obtained for the control peptide melittin. However, unlike melittin, PEP27-2 was not toxic within the range of antimicrobial activity or 4×MIC concentration. Melittin begins to show toxicity within the range of antibacterial activity that increases rapidly from 2×MIC. These results indicate that PEP27-2 is a viable candidate, particularly for human pathogenic bacteria, including MDR bacteria if developed as a novel antimicrobial drug usable at low concentrations.

5. Measurement of Circular Dichroism Spectrum

In order to confirm whether the peptide prepared by the method of above 1 form the α-helical structure, which is a secondary structure, a spectrum was measured by a circular dichroism method.

Specifically, PEP27, PEP27-1, PEP27-2 or PEP27-5 peptide in a suspension of 1 mM large unilamellar vesicles

TABLE 5

| | Erythrocyte destruction ability (%) | | | | | |
|---|---|---|---|---|---|---|
| | Peptide concentration 100 μM | Peptide concentration 50 μM | Peptide concentration 25 μM | Peptide concentration 12.5 μM | Peptide concentration 6.25 μM | Peptide concentration 3.13 μM |
| PEP27 (SEQ ID NO: 1) | 3.58 | 3.64 | 2.76 | 1.79 | 1.26 | 0 |
| PEP27-1 (SEQ ID NO: 2) | 50.65 | 44.51 | 25.75 | 1.97 | 1.05 | 0 |
| PEP27-2 (SEQ ID NO: 3) | 75.84 | 62.47 | 40.51 | 14.96 | 2.30 | 0 |
| PEP27-5 (SEQ ID NO: 4) | 3.25 | 2.34 | 0 | 0 | 0 | 0 |
| Buforin 2 | 5.77 | 3.10 | 2.05 | 0.92 | 0.29 | 0 |
| Melittin | 99.17 | 97.76 | 83.99 | 69.75 | 49.41 | 27.33 |

4. Confirmation of Cytotoxicity in Normal Cell Lines

In order to confirm the cytotoxicity of the peptides prepared by the method of above 1 in normal cell lines, toxicity was tested in HaCaT (human keratinocyte fibroblasts cell, FIG. 14A) and MCF-7 (human breast adenocarcinoma cell, FIG. 14B) cells.

Specifically, Thiazolyl blue tetrazolium bromide (MTT, Merck KGaA) was used to determine the cytotoxicity of PEP27 and its analogs against HaCaT (human keratinocyte fibroblasts, n=4 per condition) and MCF-7 (human breast adenocarcinoma, n=3 per condition) cells. The cells were cultured in Dulbecco's modified Eagle's medium (DMEM) supplemented with 10 heat-inactivated fetal bovine serum (FBS, Gibco, Grand Island, NY, USA) and 1% penicillin-streptomycin (Gibco) at a density of 2×10⁴ cells/well (96-well plate). Peptides were then added at various concentrations and incubated for 24 h at 37° C., after which MTT (final concentration, 0.5 mg/mL) was added to each well and incubated for 4 h. The formazan product was solubilized in DMSO, and the absorbance at 570 nm was measured to induce cytotoxicity. Cells treated with 0.1% Triton X-100 were used as the 100% cytotoxic control sample.

Figure 14A:
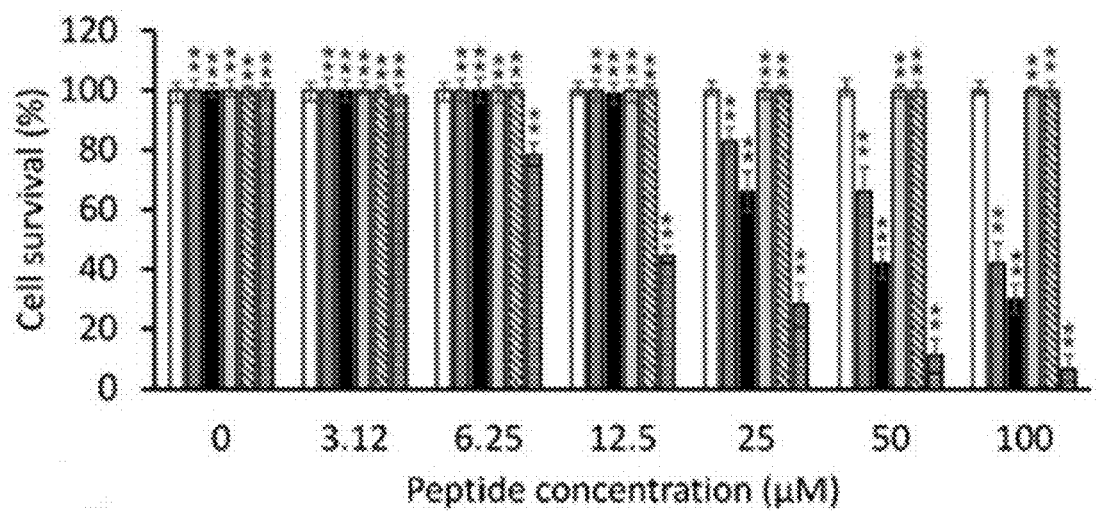
FIGS. 14A and 14B illustrate the dose-response curve for cytotoxic activity against HaCaT (FIG. 14A) (n=4 per condition) and MCF-7 (FIG. 14B) (n=3 per condition) cells. Symbols represent mean±SD from triplicate determinations. Data in FIGS. 14A and 14B were analyzed by two-way ANOVA. **$P<0.01$.
Figure 14B:
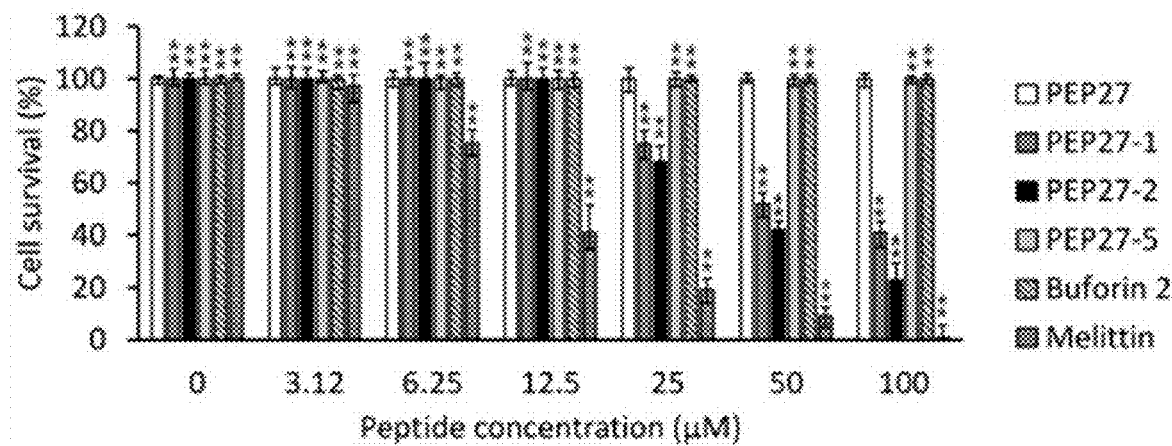

As a result, as shown in FIGS. 14A and 14B, at a high concentration of 100 μM, the cell viabilities following (LIV) that consists of 10 mM PBS (pH 7.4), PE/PG (L-α-phosphatidylethanolamine/L-α-phosphatidyl-DL-glycerol; 7/3, w/w) or PC/CH/SM (L-α-phosphatidylcholine/cholesterol/sphingomyelin; 1/1/1, w/w/w) was added at 40 μM to a cell of 0.1 cm length (path-length) and fixed, followed by measuring a circular dichroism spectrum on a Jasco 810 spectrophotometer at a temperature of 25° C. The α-helical structure calculation formula for the circular dichroic spectrum was used in Equation 2 below.

$$[\theta] = \frac{\theta_{obs}}{10 \cdot l \cdot c}$$  [Equation 2]

(wherein $\theta_{obs}$ represents millidegrees of a signal, l represents an optical path-length of a cell size (cm), and c represents a concentration (mol/L) of added peptide).

As a result, when the peptide was added to the 10 mM PBS solution, no structure was formed, whereas, when the peptide was added to the LUV solution consisting of PE/PG (7/3) or PC/CH/SM (1/1/1), it could be seen that the α-helix structure, which is a secondary structure, was formed in all peptides even with difference in structures therebetween.

From the results, it was confirmed that the antimicrobial peptide of the present invention could form the α-helical structure on a PE/PG (7/3) solution similar to a membrane of bacteria, which is a microorganism and a PC/CH/SM (1/1/1) solution similar to an eukaryotic membrane (FIGS. 1A to 1C).

6. Cell Membrane Disruption

To investigate the interactions with the peptide-bacterial cell membrane, we estimated the permeability of PEP27-2 in *E. coli* cytoplasmic membranes producing β-galactosidase.

Changes in the permeability of the inner membrane of *E. coli* caused by the peptides were estimated by measuring β-galactosidase activity using o-nitrophenyl-β-galactosidase (ONPG, Merck KGaA, n=3 per condition) as a substrate, as described previously. Mid-log-phase *E. coli* ATCC 25922 cells were washed with 10 mM PBS (pH 7.4) containing 100 mM NaCl and resuspended in 10 mM PBS (pH 7.4) to an $OD_{600}$ of 1.2. The cell suspension was incubated with 1 mM ONPG and 1×MIC of the peptides. Fluorescence was measured at excitation and emission wavelengths of 622 and 670 nm, respectively. Time-dependent changes in the relative fluorescence intensity at 420 nm were measured with a Versa-Max microplate reader (Molecular Devices, Sunnyvale, CA, USA).

Figure 15A:
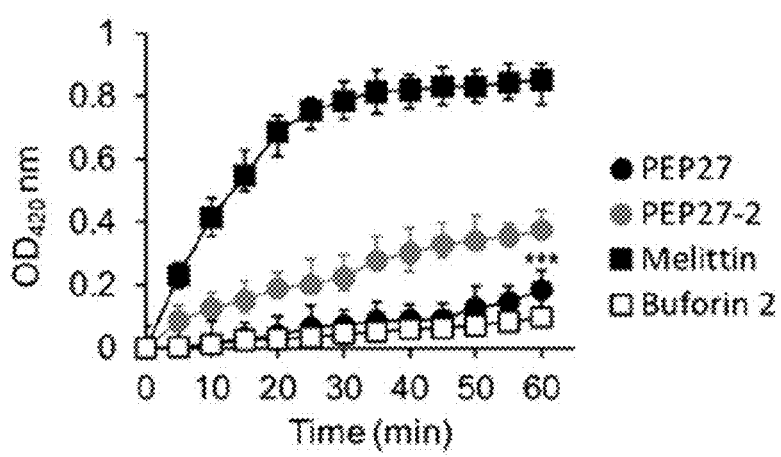
FIGS. 15A to 15E illustrate the effect of PEP27 and PEP27-2 on bacterial membrane permeability.
Figure 15B:
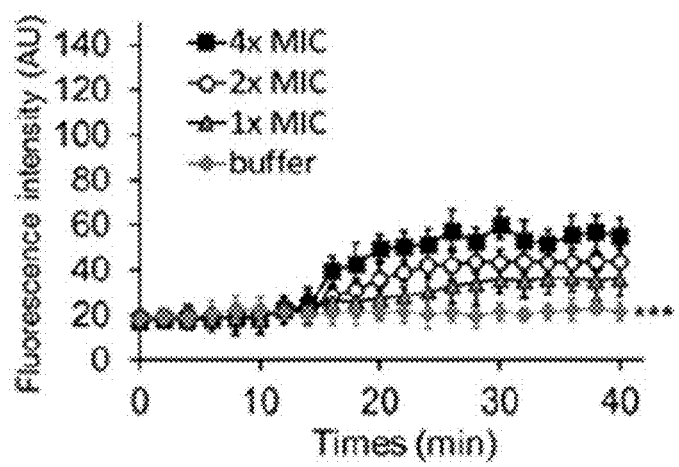
Figure 15C:
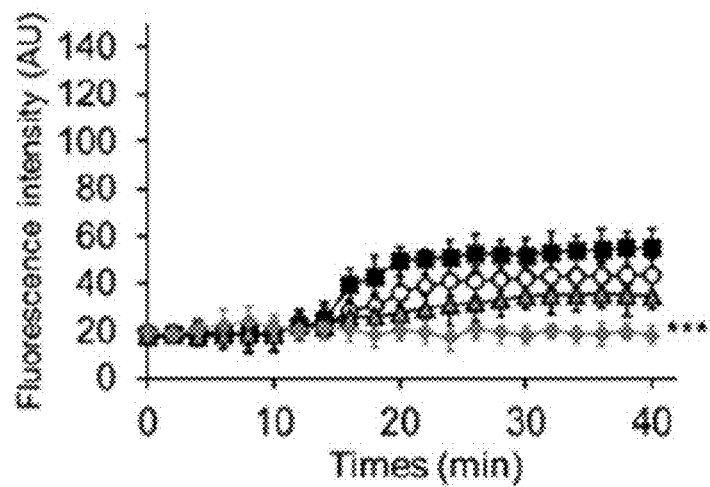
Figure 15D:
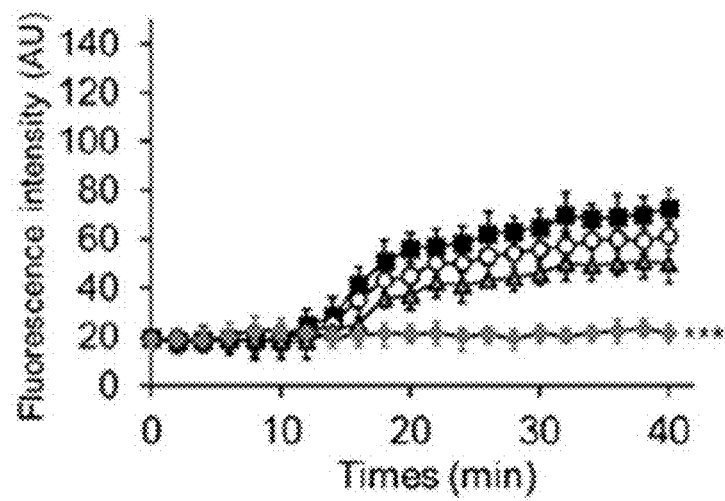
Figure 15E:
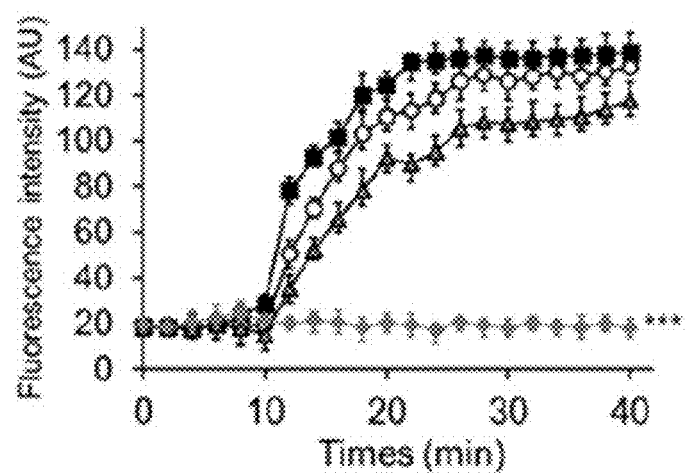

As shown in FIG. 15A, PEP27 did not permeate the inner membrane at the MIC. PEP27-2 slightly induced inner membrane permeabilization compared to PEP27 at its MIC. However, the membrane-permeable activity of PEP27-2 was weak compared to that of melittin peptides. Melittin at the MIC rapidly increases the permeabilization of the bacterial inner membrane. This finding indicates that PEP27-2 did not completely destroy the cytoplasmic membranes when killing *E. coli*.

We also used *E. coli* cells and the membrane potential-sensitive cyanine dye 3,3'-dipropylthiadicarbocyanine iodide ($DiSC_3$-5) to test the ability of PEP27 and PEP27-2 to depolarize Gram-negative bacterial membranes (FIG. 15B to FIG. 15E).

Depolarization of the cytoplasmic membrane by the peptides was measured using the membrane potential-sensitive dye $DiSC_3$-5 (Merck KGaA, n=4 per condition) with intact *E. coli* cells as previously described. 66 Mid-log-phase *E. coli* ATCC 25922 cells were washed with 5 mM HEPES buffer containing 20 mM glucose and resuspended to an $OD_{600}$ of 0.05 in 5 mM HEPES buffer containing 20 mM glucose and 0.1 M KCl. The cell suspension was incubated with 1 µM $DiSC_3$-5 for 1 h. Next, 1×, 2×, and 4×MIC of PEP27-2 was added to the mixture of *E. coli* cells and $DiSC_3$-5. Fluorescence was measured at excitation and emission wavelengths of 622 and 670 nm, respectively.

When the bacterial cytoplasmic membrane is disrupted, the membrane potential dissipates *E. coli*, and $DiSC_3$-5 is released into the culture medium, resulting in a fluorescence increase. After stabilization for 10 min by treatment with $DiSC_3$-5, AMPs were added, and the plasma membrane potential of *E. coli* was confirmed by monitoring the change in fluorescence intensity for another 30 min.

When cells were treated with PEP27-2 and melittin, the fluorescence intensity increased dose-dependently. This suggests a significant membrane depolarization effect in *E. coli*. Melittin at 4×MIC showed an increase in fluorescence intensity to nearly 140, whereas 4×MIC of PEP27 and PEP27-2 increased the fluorescence intensity only up to 80. PEP27 and PEP27-2 showed very similar results as the control (buffer), suggesting that minimal membrane depolarization is involved in membrane interactions.

7. AMP-Induced Calcein Release in LUVs

To examine the mechanism of action of PEP27 and PEP27-2, we evaluated the changes in bacterial cell membrane permeability by monitoring the release of calcein, a fluorescent marker, from calcein entrapped LUVs with different lipid bilayer compositions.

Peptide-induced membrane permeabilization was quantified by monitoring calcein release from LUVs (n=3 per condition). Different calcein-entrapped LUVs [PE/PG (7/3) or PC/CH/SM (1/1/1)] were prepared as described above, except that the dry lipid films were resuspended in 1 mL of PBS (pH 7.2) containing 70 mM calcein. Gel filtration chromatography on a Sephadex G-50 column was performed to separate free calcein from that entrapped in LUVs. Thereafter, the LUVs with entrapped calcein were mixed with peptides at various ratios, and the fluorescence of the released calcein was measured with a SpectraMax M3 Multi-Mode Microplate Reader (Molecular Devices, Sunnyvale, CA, USA) at excitation and emission wavelengths of 480 and 520 nm, respectively. The results obtained for a sample treated with 0.1% Triton X-100 were considered complete (100%) release.

Figure 16A:
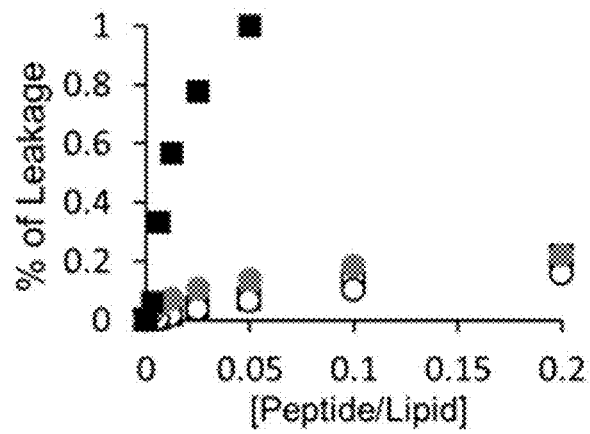
FIGS. 16A and 16B illustrate the Calcein release from PE/PG (7/3, w/w) (FIG. 16A) and PC/CH/SM (1/1/1, w/w/w) (FIG. 16B) LUVs induced by PEP27 and PEP27-2 (n=3 per condition).
Figure 16B:
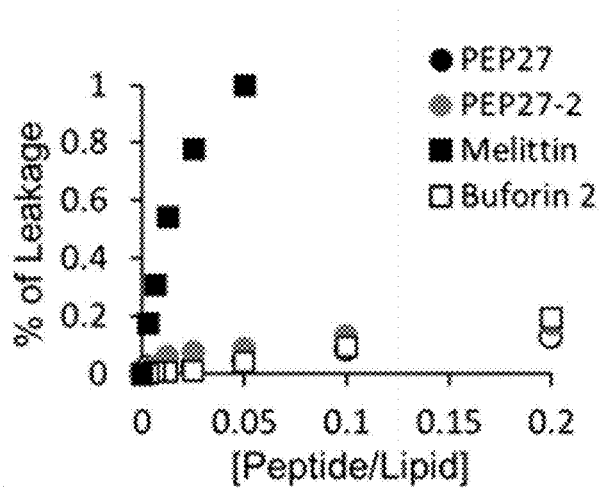

The results are shown in FIGS. 16A and 16B. PEP27, PEP27-2, and CPP buforin 2 induced little or no calcein release from the PE/PG and PC/CH/SM LUVs. Even at high peptide-to-lipid (P/L) ratios of 0.2, PEP27, PEP27-2, and buforin 2 only caused leakage (12%, 20%, and 20%, respectively) in the PE/PG and PC/CH/SM liposomes. The positive control melittin (a pore-forming AMP) induced maximum leakage of 100% at a P/L ratio of 0.05 (FIGS. 16A and 16B). These results confirm that PEP27-2 does not destroy the bacterial cell membrane and killed bacteria via other mechanisms.

8. Flow Cytometry Measurement

In order to confirm whether the peptide prepared by the method of above 1 acts on the bacterial membrane, PEP27-2 peptide having better antimicrobial activity than the parental peptide was analyzed through flow cytometry.

Specifically, the minimal inhibitory concentration (MIC) values of the PEP27 parental peptide or the PEP27-2 peptide were used for treatment of *E. coli*, respectively, followed by reaction at 37° C. for 1 hour. Thereafter, the supernatant was removed using a centrifuge (10,000 rpm) and stained with propidium iodide (PI) at a concentration of 10 µg/ml at 4° C. for 30 minutes. Then, the unbound propidium iodide (PI) was removed using the centrifuge, and 1 ml of physiological saline (PBS) was added to remove agglomeration of the cells. Thereafter, effects of the peptide on the bacterial membrane were determined using a Bechman flow cytometer.

Figure 2:
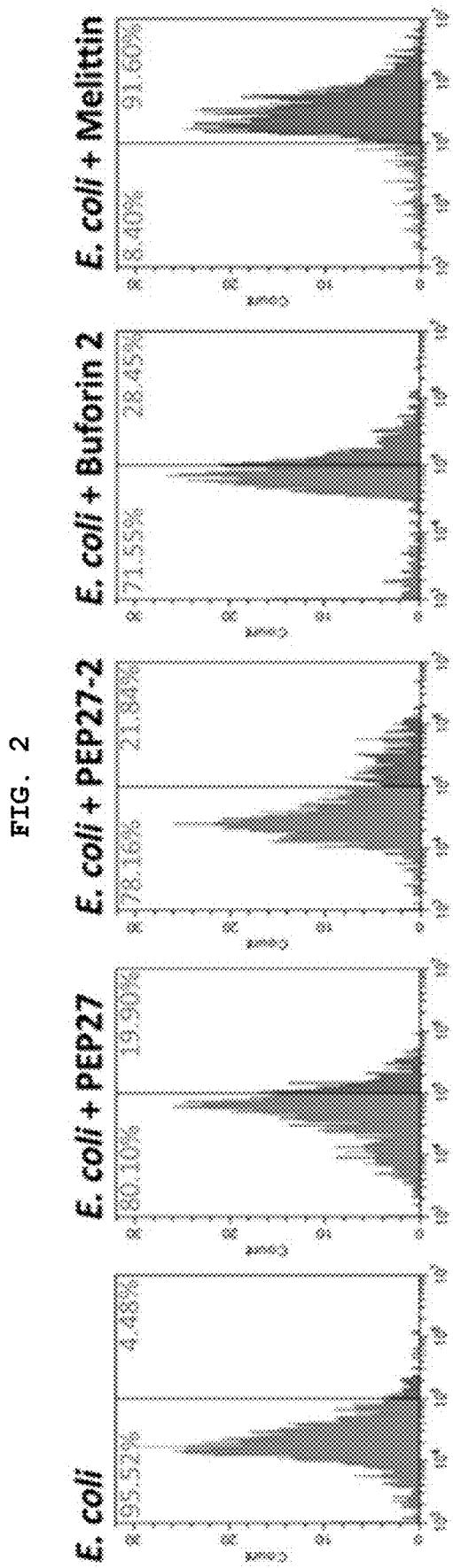
FIG. 2 illustrates results of confirming the action of PEP27 peptide as the control and PEP27-2 as the new peptide, respectively, on *Escherichia coli* membrane by flow cytometry (FACS)

As a result, as shown in FIG. 2, it was confirmed that the PEP27-2 peptide (21.84%) was a little superior to the PEP27 parental peptide (19.9%) in terms of membrane destruction ability in *Escherichia coli* cell. For the positive control without peptides, the percentage of PI-positive *E. coli* cells was very low (4.48%), indicating that the bacterial cell membranes were intact. However, like buformin 2 as a cell permeable peptide, the above peptides were found not to have an ability of damaging a bacterial membrane. It was confirmed that PEP27 and PEP27-2 could extinct *Escherichia coli* without destruction of the *E. coli* membrane. Among control peptides, melittin destructing a cell membrane was found to have cell membrane destruction ability in *Escherichia coli*, therefore, the peptide of the present invention was demonstrated to have a mechanism different from that of melittin.

9. Analysis of Binding of Antimicrobial Peptide and DNA

In order to specifically determine what mechanism the synthetic peptide of the present invention prepared by the method of above 1 exhibits antimicrobial activity, it was investigated through electrophoresis whether PEP27, PEP27-1, PEP27-2 or PEP27-5 synthetic peptide binds to DNA, which is an internal material of bacteria.

Specifically, 300 ng of plasmid DNA (pRSETB) was reacted with the peptide by a relative ratio (reactions were performed at peptide/DNA ratios of DNA alone, 0.25:1, 0.5:1, 1:1, 1.5:1, 2:1, 3:1, 4:1, respectively) at 37° C. for 10 minutes, followed by conducting electrophoresis on a 1% agarose gel, staining the same with ethidium bromide (EtBr) and monitoring through UV.

Figure 3:
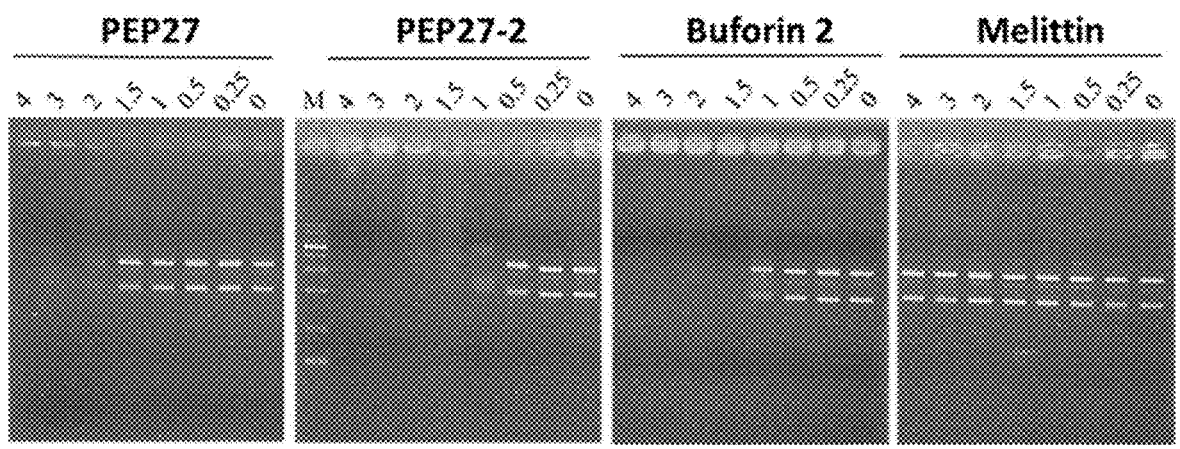
FIG. 3 illustrates results of confirming the binding ability of PEP27 peptide as the control and PEP27-2 as the new peptide, respectively, to DNA, which is an internal substance of bacteria, wherein the ratio of peptide:DNA is DNA alone (0), 0.25:1, 0.5:1, 1:1, 1.5:1, 2:1, 3:1 and 4:1, respectively.

As a result, as shown in FIG. 3, melittin as a comparison peptide was not bound to any DNA, while all the PEP27, PEP27-2 and the control peptide were bound to DNA even with difference in binding levels (FIG. 3). Herein, PEP272-2 peptide showed DNA binding ability higher than PEP27. From the above results, it was confirmed that, due to substitution of some amino acid residues, PEP27-2 peptide has higher binding ability to DNA, which is an internal material of bacteria, as compared to the parental peptide, thereby exhibiting higher antimicrobial activity.

10. Scanning Electron Microscope (SEM) Analysis

In order to confirm whether the synthetic peptides of the present invention prepared by the method of above 1 would damage the bacterial cell membrane, it was investigated through a scanning electron microscope.

Specifically, after suspending E. coli and Staphylococcus aureus cells in PBS at a concentration of 0.2 in terms of $OD_{600}$, the cells were treated with PEP27-2 peptide at MIC and then reacted at 37° C. for 1 hour. As a control, a strain not treated with peptide was used. After incubation, the cells were recovered, treated with 2.5% glutaraldehyde at 4° C. for 18 hours, and washed twice with PBS buffer solution. The fixed cells were dehydrated for 10 minutes using 100% ethanol and diluted ethanol (50%, 70%, 90% and 100%) in sequential order, and then the samples were dried and coated with platinum, followed by observation through a low vacuum scanning electron microscope.

Figure 4:
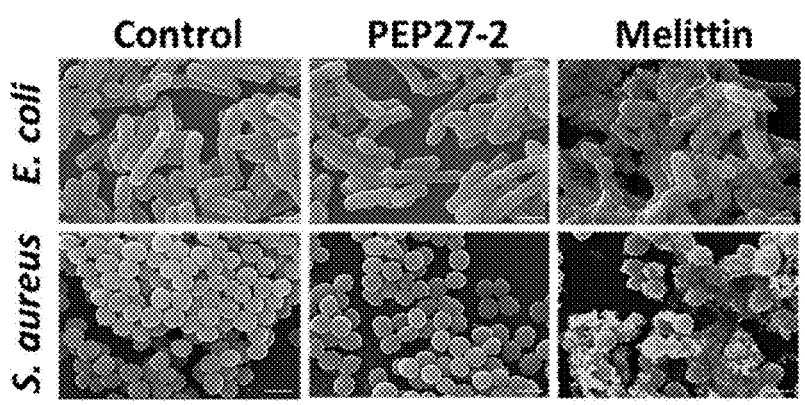
FIG. 4 illustrates results of confirming the action of PEP27 peptide as the control and PEP27-2 as the new peptide, respectively, on *Staphylococcus aureus* membrane by a scanning electron microscope (SEM)

As a result, as shown in FIG. 4, it was confirmed that the peptide-untreated control cells had a bright and smooth surface whereas the cells treated with melittin, which is a membrane destruction peptide used as a comparison control, showed significant membrane damage. The cell surface exposed to the peptide was observed to have blister-like damage due to formation of pores and, in some cases, leakage of contents in the cytoplasm was observed. However, the cells treated with PEP27-2 peptide appeared very little cell damage, which is almost the same as the control. As a result, it was confirmed that bacteria became extinct without destruction of the cell membrane.

11. Cell Absorption of Peptide

With regard to the synthetic peptide prepared by the method of above 1, an ability of penetrating cells was determined through a phase-contrast microscope. Specifically, human keratinocyte line (HaCaT cells) was dispensed on a 6-well plate provided with a polylysine coating cover slip (SPL Life Sciences, Gyeonggi-do, Korea) at $2 \times 10^5$ cells/well and cultured for 24 hours, and then treated with fluorescein isothiocyanate (FITC)-labeled PEP27-2 (FITC-PEP27-2) at a concentration of 5 µM, followed by incubation in a 5% $CO_2$ incubator for 1 hour. After 1 hour, a nucleus of the cell was treated and stained with Hoechst 33342 nucleic acid dye solution (Invitrogen, Carlsbad, CA, USA; 8 µM) for 10 minutes. After washing the stained product with PBS three times, fluorescence in the cells was imaged using a phase-contrast microscope (EVOS™ FL Auto 2 Imaging System, Thermo Fisher Scientific).

Figure 5:
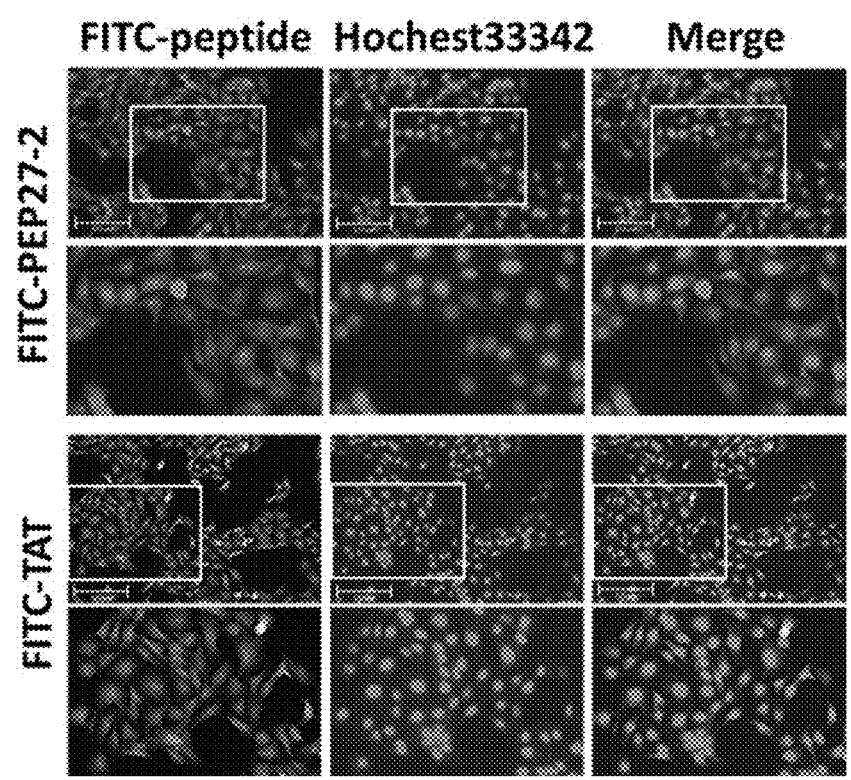
FIG. 5 illustrates results of confirming internalization of PEP27-2 peptide labeled with FITC on human keratinocyte line (HaCaT cell line, Dr. N E. Fusenig, Heidelberg, Germany) (FITC-PEP27-2) by a fluorescence microscope.

As a result, as shown in FIG. 5, FITC-PEP27-2 was obviously absorbed in HaCaT cells and uniformly distributed as green fluorescence in the cells, thus appearing in both of the cytoplasm and the nucleus. In order to confirm localization of PEP27-2 in the nucleus, contrast staining of the nucleus of the cell treated with FITC-labeled peptide was performed with a nucleus staining dye Hoechst 33342. From the stained cell, it was confirmed that PEP27-2 is distributed in both of the cytoplasm and the nucleus of HaCaT cells. And in HaCaT cells, cellular absorption of FITC-PEP27-2 into the cytoplasm and the nucleus was confirmed. On the other hand, the control peptide, that is, TAT (GRKKRRQRRRPQ (SEQ ID NO:5)) which is a cell permeable peptide having 11 amino acid residues and is highly positive-charged, was found to be absorbed into the cytoplasm and the nucleus of HaCaT cell like the PEP27-2 peptide.

12. Measurement of Anti-Biofilm Activity

Biofilms may form on a wide variety of surfaces, including living or dead surfaces, and biofilm-associated bacteria are more tolerant to antibiotics than planktonic bacterial cells, making them antibiotic-resistant. To assess the efficacy of PEP27-2 against biofilms, we observed the anti-biofilm activity of PEP27-2 in S. aureus (ATCC 25923 and CCARM 3090), E. coli (ATCC 25922 and CCARM 1238), and P. aeruginosa (ATCC 27853 and 4891).

Figure 17A:
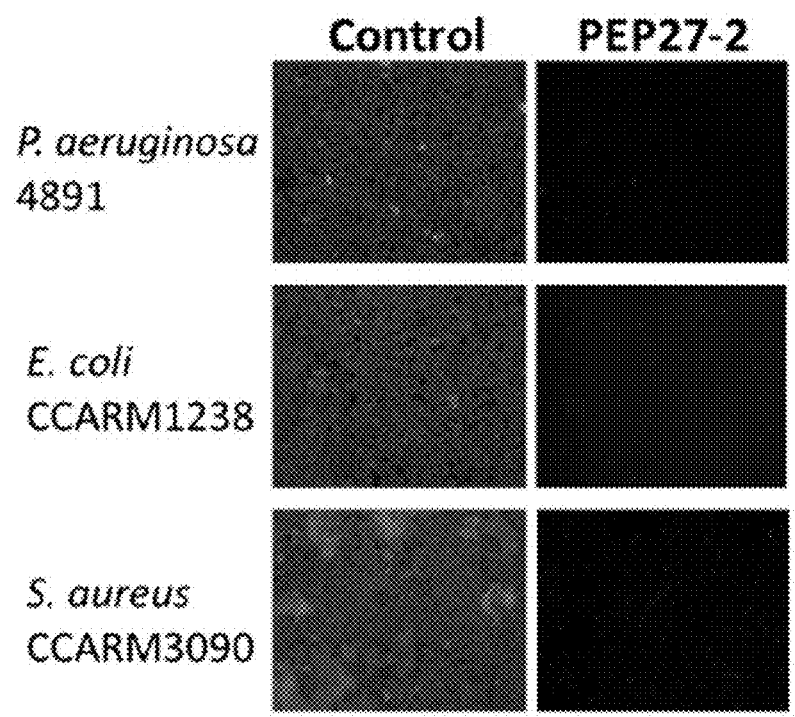
FIGS. 17A to 17C illustrate inhibition of biofilm formation.
Figure 17C:
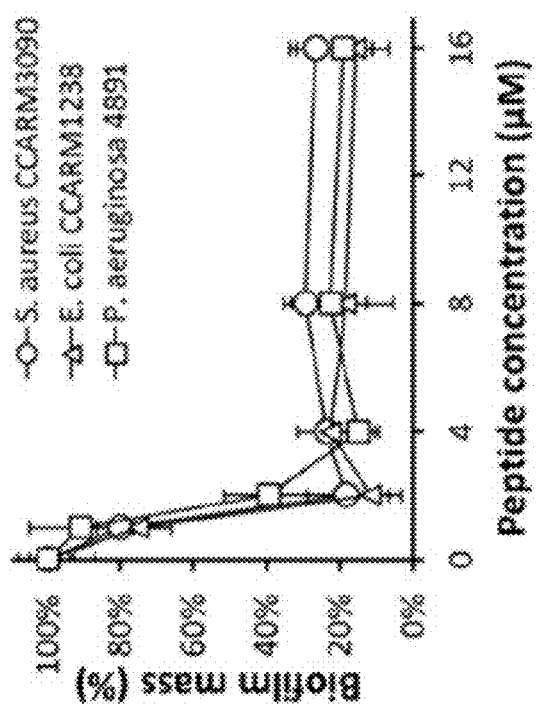
Figure 17B:
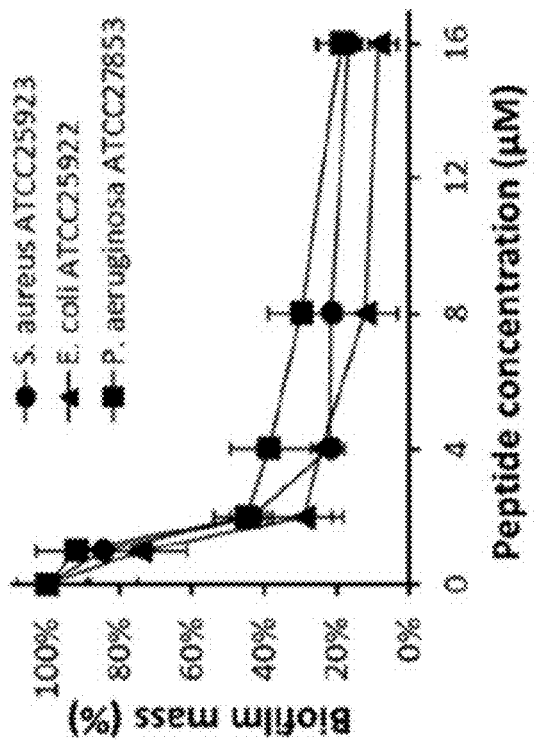

All tested bacterial strains formed widespread biofilms in the absence of PEP27-2 (FIG. 17A). The maximum percent biofilm inhibition by PEP27-2 was 83.4% against S. aureus ATCC 25923, 91.8% against E. coli ATCC 25922, and 81.2% against P. aeruginosa ATCC 27853 (FIG. 17B). In addition, we confirmed that PEP27-2 efficiently inhibits biofilm formation by MDR bacterial strains (73.3% against S. aureus CCARM 3090, 84.3% against E. coli CCARM 1238, and 81.1% against P. aeruginosa 4891) (FIG. 17C).

We also observed minimal biofilm inhibitory concentration (MBIC) against MDR S. aureus, E. coli, and P. aeruginosa.

Specifically, among the strains listed in Table 3 above, Staphylococcus aureus, E. coli and Pseudomonas erujinosa, respectively, were cultured in each medium to a mid-log phase, diluted to a cell concentration of $5 \times 10^4$ cells/100 µl, and then, inoculated into a micro-plate (SPL). Then, PEP27-2 peptide was diluted ⅒ times with 10 mM PBS solution (pH 7.2) and 10 µl of the solution was added to each well, followed by incubation at 37° C. for 24 hours. After completely removing the supernatant, the solution was fixed with 100% methanol for 15 minutes, stained with a crystal violet dye solution for 1 hour, washed 3 times, and then dissolved in 95% ethanol, followed by measuring the absorbance at a wavelength of 595 nm using a micro titration plate reader, thereby determining a biofilm minimal inhibitory concentration value for each strain.

As a result, as shown in Table 6 below, it was confirmed that PEP27-2 peptide exhibited strong biofilm inhibitory activity in all strains, which is substantially similar to that of melittin as the control peptide.

TABLE 6

| | Biofilm minimal inhibitory concentration (μM) | |
|---|---|---|
| | PEP27-2 | Melittin |
| Gram-positive bacteria | | |
| S. aureus ATCC25923 | 4 | 4 |
| S. aureus ATCC29213 | 4 | 4 |
| Gram-negative bacteria | | |
| E. coli ATCC25922 | 8 | 4 |
| E. coli ATCC27325 | 8 | 4 |
| P. aeruginosa ATCC15692 | 8 | 4 |
| P. aeruginosa ATCC27853 | 8 | 4 |

TABLE 6-continued

| | Biofilm minimal inhibitory concentration (μM) | |
|---|---|---|
| | PEP27-2 | Melittin |
| Antibiotics-tolerant gram-positive bacteria | | |
| S. aureus CCARM3089 | 4 | 4 |
| S. aureus CCARM3090 | 4 | 4 |
| S. aureus CCARM3518 | 4 | 8 |
| Antibiotics-tolerant gram-negative bacteria | | |
| E. coli CCARM1229 | 8 | 4 |
| E. coli CCARM1238 | 8 | 4 |
| P. aeruginosa 4007 | 8 | 4 |
| P. aeruginosa 4891 | 8 | 8 |

13. Confirmation of Antimicrobial Activity of Antimicrobial Peptide and Antibiotics In order to compare the antimicrobial activity of PEP27-2, which is the peptide having the most excellent antimicrobial activity among the peptides prepared by the method of above 1, with existing antibiotics, MIC concentrations of specific antibiotics were investigated with regard to the same gram-positive bacteria (Staphylococcus aureus) and the same gram-negative bacteria (Pseudomonas erujinosa) stains. Specifically, subject strains were prepared by the method of above 2, and were treated with the antibiotics, that is, meropenem, ceftazidime, ceftriaxone or vancomycin, respectively, followed by determining MICs of the antibiotics.

As a result, as shown in Table 7 below, it was confirmed that PEP27-2 express antimicrobial activity and MIC of PEP27-2 to 11 types of strains has ranged from 2 to 4 μM. Specifically, it was confirmed that meropenem, ceftazidime, ceftriaxone and vancomycin express antimicrobial activity and MICs of these antibiotics have ranged from 0.25 to 512 μM (Table 7).

| | Minimal inhibitory concentration (μM) | | | | |
|---|---|---|---|---|---|
| Microorganism | PEP27-2 | Meropenem | Ceftazidime | Ceftriaxone | Vancomycin |
| S. aureus ATCC25923 | 2 | 2 | 16 | 8 | 0.25 |
| S. aureus ATCC29213 | 2 | 2 | 3 | 4 | 0.25 |
| S. aureus CCARM3089 | 4 | 64 | 512 | 512 | 0.25 |
| S. aureus CCARM3090 | 4 | 128 | 512 | 512 | 0.5 |
| S. aureus CCARM3518 | 4 | 64 | 64 | 256 | 0.25 |
| S. aureus USA300 | 2 | 2 | 32 | 16 | 0.25 |
| S. aureus MW2 | 4 | 2 | 32 | 32 | 0.25 |
| P. aeruginosa ATCC15692 | 4 | 2 | 4 | 16 | 512 |
| P. aeruginosa ATCC27853 | 4 | 2 | 2 | 8 | 256 |
| P. aeruginosa 4007 | 4 | 4 | 16 | 16 | 512 |
| P. aeruginosa 4891 | 4 | 8 | 16 | 64 | 512 |

14. Confirmation of Synergistic Effects of Combination Treatment of Antimicrobial Peptide and Antibiotics Based on MIC values determined with regard to respective mixtures, synergistic effects of the peptide and the antibiotics in relation to antimicrobial activity to strains were assessed. For assessment, fractional inhibitory concentration (FIC) analysis was implemented by checkerboard assay.

Specifically, after inoculating 100 μl of bacteria ($5×10^5$ CFU/mL) to each well of a 96-well plate, 50 μl of peptide solution diluted from the MIC value (solution 2:1 diluted by stages) was added to each well. Thereafter, an antibiotic solution was diluted and added to each well by 50 μl. Further, the above procedures were implemented under opposite conditions, so as to determine MIC value of each mixed solution. FIC values were calculated as follows: FIC index=FIC (A)+FIC (B)=[A]/MIC (A)+[B]/MIC (B), wherein [A] represents the MIC of PEP27-2 when used in combination with antibiotics, MIC (A) represents the MIC of PEP27-2 alone, FIC (A) represents FIC of PEP27-2, and [B], MIC (B) and FIC (B) represent values corresponding to the antibiotics. With the calculated FIC values, it was assessed as follows: <0.5—synergy effect; 0.5 to 4—indifference; >4.0—antagonism.

Figure 18B:
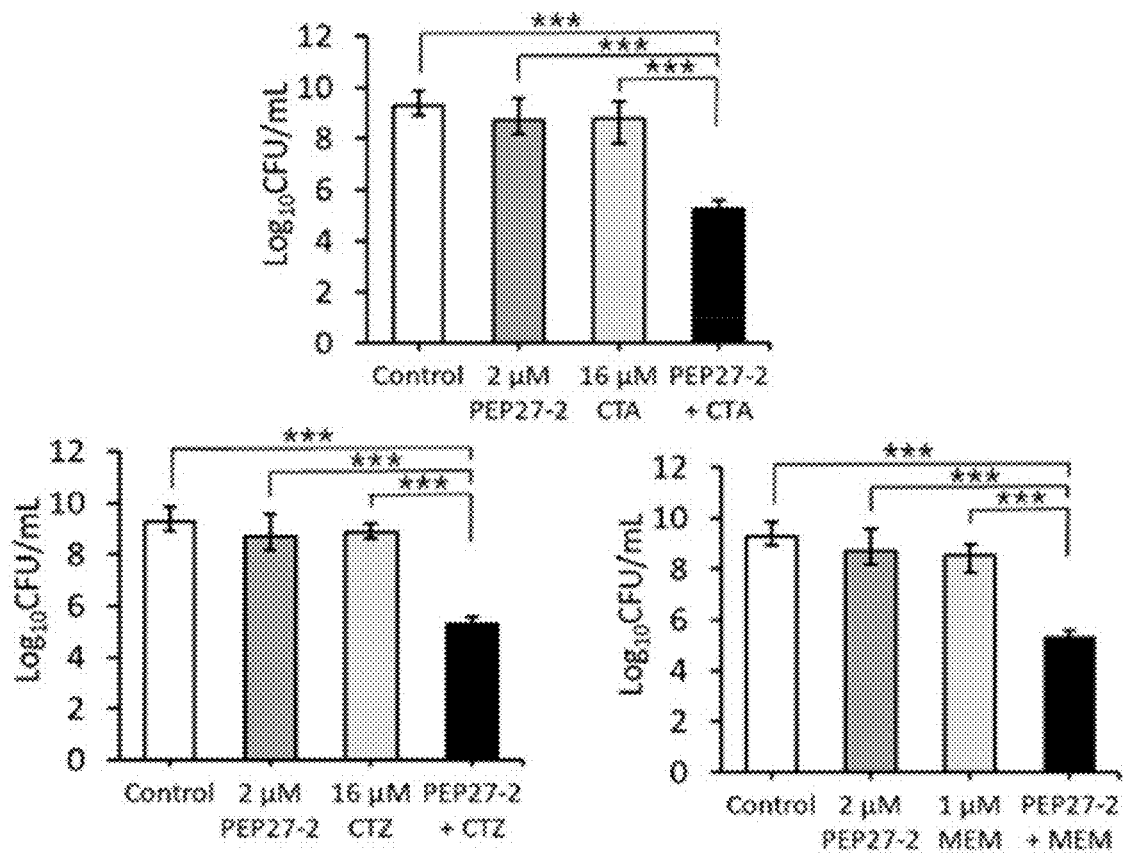
Figure 18C:
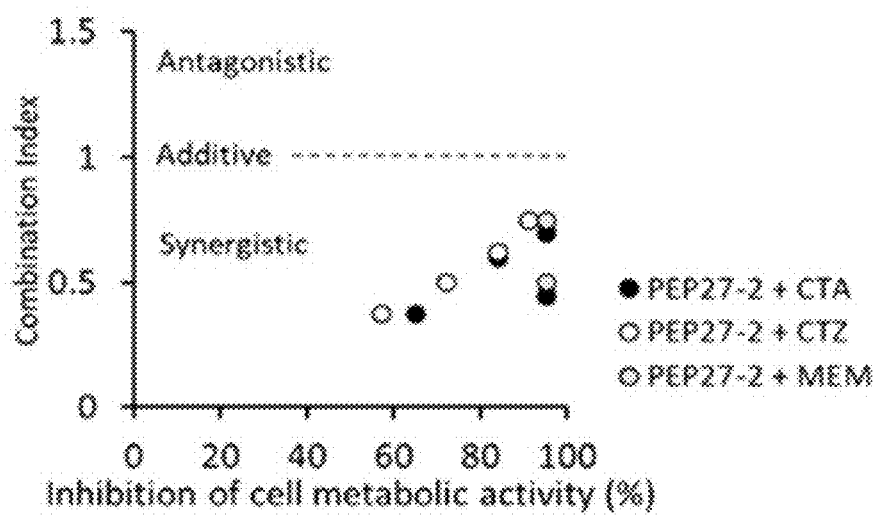

As a result, it was confirmed that any combination of the peptide and the antibiotics did not appear antagonism. Accordingly, as shown in Table 8 below and FIGS. 18A to 18C, with regard to *Staphylococcus aureus* CCARM 3089 and CCARM 3090, synergistic effects were demonstrated when meropenem, ceftazidime or ceftriaxone was combined with 0.25×MIC of PEP27-2. Further, with regard to *Pseudomonas erujinosa* 4891 and *Staphylococcus aureus* MW2, synergistic effects were demonstrated only when either meropenem or ceftriaxone was combined with 0.25× MIC of PEP27-2 (Tables 8 and 9). As shown in Tables 9 and 10 below, synergistic effects were expressed in most of antibiotics-tolerant strains as compared to a few of standard strains.

TABLE 8

| Strain | Treated peptide/antibiotics | Fractional inhibitory concentration (FIC) | Effects of combination |
| --- | --- | --- | --- |
| S. aureus ATCC2523 | PEP27-2/Meropenem | 1 | Indifferent |
| | PEP27-2/Ceftazidime | 0.75 | Indifferent |
| | PEP27-2/Ceftriaxone | 0.75 | Indifferent |
| S. aureus ATCC29213 | PEP27-2/Meropenem | 1 | Indifferent |
| | PEP27-2/Ceftazidime | 0.75 | Indifferent |
| | PEP27-2/Ceftriaxone | 0.75 | Synergy |
| S. aureus USA300 | PEP27-2/Meropenem | 0.75 | Indifferent |
| | PEP27-2/Ceftazidime | 0.75 | Indifferent |
| | PEP27-2/Ceftriaxone | 0.75 | Indifferent |
| S. aureus MW2 | PEP27-2/Meropenem | 0.5 | Synergy |
| | PEP27-2/Ceftazidime | 0.75 | Indifferent |
| | PEP27-2/Ceftriaxone | 0.5 | Synergy |
| S. aureus CCARM3089 | PEP27-2/Meropenem | 0.5 | Synergy |
| | PEP27-2/Ceftazidime | 0.5 | Synergy |
| | PEP27-2/Ceftriaxone | 0.5 | Synergy |
| S. aureus CCARM3090 | PEP27-2/Meropenem | 0.38 | Synergy |
| | PEP27-2/Ceftazidime | 0.5 | Synergy |
| | PEP27-2/Ceftriaxone | 0.5 | Synergy |
| S. aureus CCARM3518 | PEP27-2/Meropenem | 0.75 | Indifferent |
| | PEP27-2/Ceftazidime | 0.75 | Indifferent |
| | PEP27-2/Ceftriaxone | 0.75 | Indifferent |

TABLE 9

| Strain | Treated peptide/antibiotics | Fractional inhibitory concentration (FIC) | Effects of combination |
| --- | --- | --- | --- |
| P. aeruginosa ATCC15692 | PEP27-2/Meropenem | 0.63 | Indifferent |
| | PEP27-2/Ceftazidime | 0.75 | Indifferent |
| | PEP27-2/Ceftriaxone | 0.5 | Synergy |
| P. aeruginosa ATCC27853 | PEP27-2/Meropenem | 0.75 | Indifferent |
| | PEP27-2/Ceftazidime | 1 | Indifferent |
| | PEP27-2/Ceftriaxone | 0.75 | Indifferent |
| P. aeruginosa 4007 | PEP27-2/Meropenem | 0.75 | Indifferent |
| | PEP27-2/Ceftazidime | 0.5 | Synergy |
| | PEP27-2/Ceftriaxone | 0.5 | Synergy |
| P. aeruginosa 4891 | PEP27-2/Meropenem | 0.5 | Synergy |
| | PEP27-2/Ceftazidime | 0.75 | Indifferent |
| | PEP27-2/Ceftriaxone | 0.5 | Synergy |

15. Measurement of Healing Ability of Abscess Infected with Multidrug-Tolerant *Staphylococcus aureus*

The efficacy of PEP27-2, which is the peptide having the most excellent antimicrobial activity among the peptides prepared by the method of above 1 was evaluated in vivo using a mouse model.

Specifically, the epidermis on the back side (dorsal side) of 6-7 week old BALB/c mouse was infected with *Staphylococcus aureus* MW2 having GFP gene inserted therein (*S. aureus* MW2-GFP, $1\times10^9$ CFU/10 µl PBS). After 2 hours form infection, PEP27-2 alone (0.2 mg/kg, 50 µl), ceftriaxone alone (0.2 mg/kg, 50 µl) or a combination of the peptide and the antibiotic (0.05 mg/kg PEP27-2+0.1 mg/kg ceftriaxone, 50 µl) was injected. Further, the control mice were injected with the same amount of PBS (20 µl) without peptide. On $1^{st}$, $2^{nd}$, $3^{rd}$, $4^{th}$, $5^{th}$ and $7^{th}$ days after treatment, the shape of abscess was photographed, and surrounding tissues as well as the abscess were gathered. The abscess tissue was homogenized in 500 µl of sterile PBS using a tissue grinder. A serial diluted solution of the homogenate was spread on an agar plate and cultured for 24 hours in order to quantify the *Staphylococcus aureus* MW2 strain.

Figure 6:
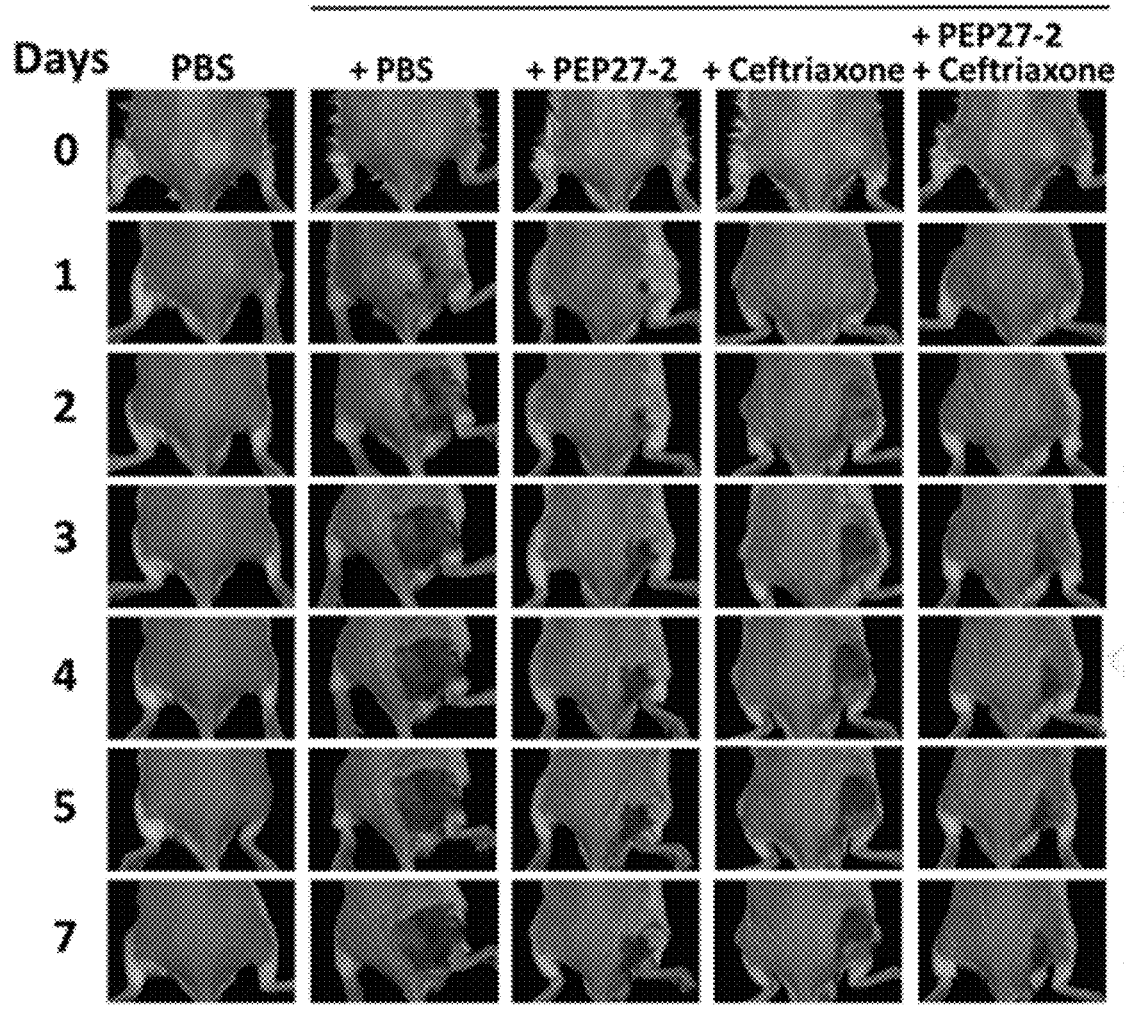
FIG. 6 illustrates results of confirming the healing effects of PEP27 peptide and antibiotics, that is, ceftriaxone, when used alone or in combination with the same for treatment of abscess formed after infection with *Staphylococcus aureus* MW2 which is a multidrug-tolerant strain.
Figure 7:
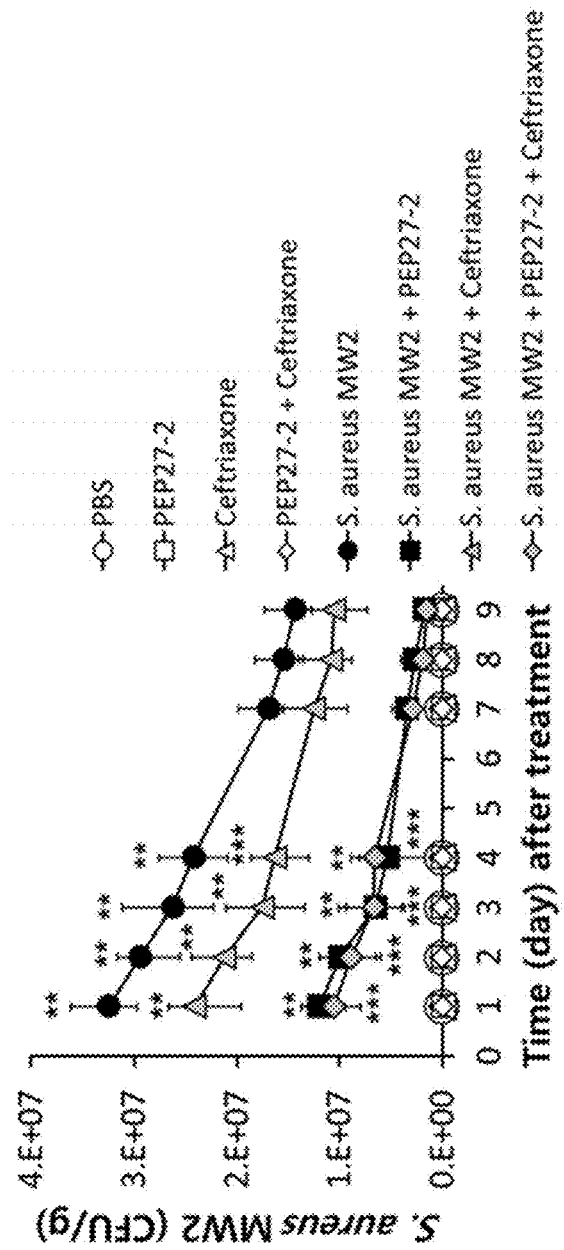
FIG. 7 illustrates results of determining a total number of bacteria (CFU/g) recovered by gathering abscess portions formed after infection with *Staphylococcus aureus* MW2 which is a multidrug-tolerant strain.

As a result, it was confirmed that abscess is not formed in the experimental group to which only PBS was injected without infection of *Staphylococcus aureus* MW2 strain (FIG. 6) On the other hand, for the experimental group to which only PBS was injected after infection of *Staphylococcus aureus* MW2, it could be seen that abscess was formed on day 1 after infection, a size of the abscess did not decrease till $7^{th}$ day, which in turn caused severe inflammation. However, in all of the experimental groups in which only PEP27-2 was injected, only ceftriaxone was injected, and a combination of PEP27-2+ceftriaxone was injected, respectively, after infection of *Staphylococcus aureus* MW2, it could be seen that the size of formed abscess was smaller than the experimental group in which only PBS was injected. On the other hand, it was confirmed visually that abscess healing effects when treated with the combination described above were significantly similar to or slightly better than treatment using PEP27-2 alone, after infection of *Staphylococcus aureus* MW2 (FIG. 6). In order to confirm the abscess healing effects more obviously, a homogenate of abscess tissue was cultured followed by counting the number of bacteria. Even from these results, it was demonstrated that, when treated using PEP27-2 or ceftriaxone after bacterial infection, the number of bacteria was reduced by 80.0% or 46.0% on day 3, respectively, and was further reduced by 89.3% or 61.5% on day 7, respectively. In addition, it was confirmed that the number of colonies after combination treatment was about 91.1%, and thus the number of *Staphylococcus aureus* MW2 strains was lower than that after single treatment (FIG. 7). Therefore, it could be understood that the combination treatment has synergistic effects of improving the removal of bacteria on infected site, as compared to the single treatment using PEP27-2 or ceftriaxone alone. Furthermore, it was confirmed that strains in the abscess portion could be effectively removed even with treatment using PEP27-2 alone.

16. Live Fluorescence Imaging of Abscess Mouse Model

For real-time tracking the progress of infection with regard to the peptide that has the most excellent antimicrobial activity among the peptides prepared by the method of above 1, fluorescence (GFP)-labeled *Staphylococcus aureus* MW2 (*Staphylococcus aureus* MW2-GFP) was used. Fluorescence images were taken from the beginning of infection to 6 hours, 1 day, 2 days and 3 days by means of an FOBI fluorescence imaging system (Neo Science, Suwon, Korea), followed by analysis thereof using live image software.

Figure 8:
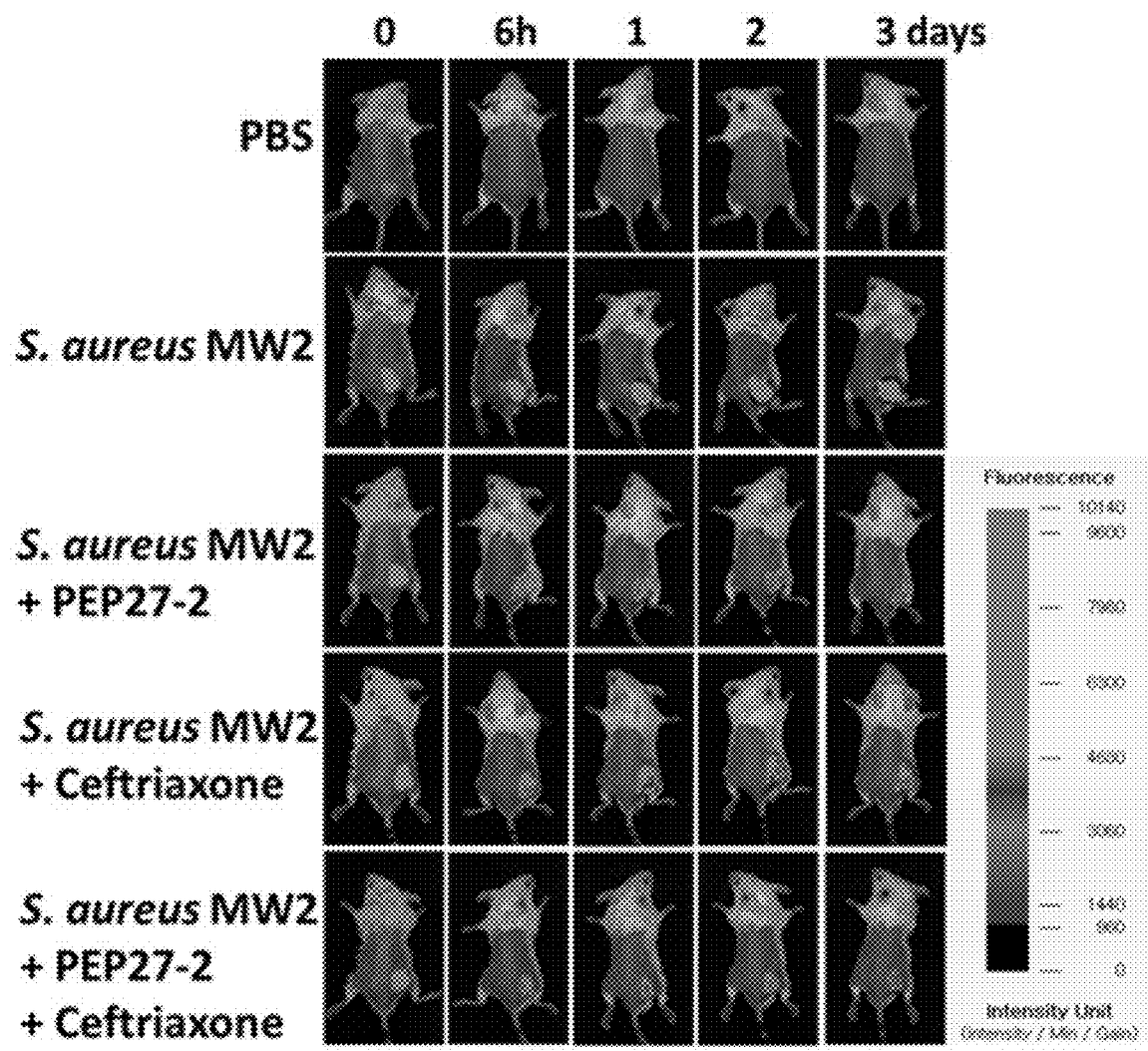
FIG. 8 illustrates results of confirming strain distribution as well as the healing effects of PEP27 peptide and antibiotics, ceftriaxone, when used alone or in combination with the same for treatment of abscess formed after infection with the strain formed by inserting green fluorescent protein (GFP) gene into *Staphylococcus aureus* MW2 which is a multidrug-tolerant strain (*Staphylococcus aureus* MW2-GFP)

As a result, on 0 hour after infection of *Staphylococcus aureus* MW2-GFP at a high dose of ($1\times10^9$ CFU), there was no difference in fluorescence signals between the experimental groups (FIG. 8). Further, on the skin surface above the abscess treated only with *Staphylococcus aureus* MW2-GFP, the fluorescence signal was continuously increased for 3 days. On the other hand, the fluorescence signal after treatment using PEP27-2 alone was substantially similar to that obtained after combination treatment, whereas the fluorescence signal after treatment using ceftriaxone alone was not reduced (FIG. 8). On the basis of the fluorescent abscess portion, it was confirmed that the combination treatment of PEP27-2 and ceftriaxone showed synergistic effects.

17. Staining of Abscess Tissue Fragment Infected with Multidrug-Tolerant *Staphylococcus aureus*

Among tissues on the abscess portion and infected portion gathered in the above 13, the tissue on day 7 was fixed with 4% buffered formalin. The infection portion or abscess portion fixed with formalin was embedded in paraffin, while staining a fragment of the cross-section with hematoxylin and eosin.

Figure 9:
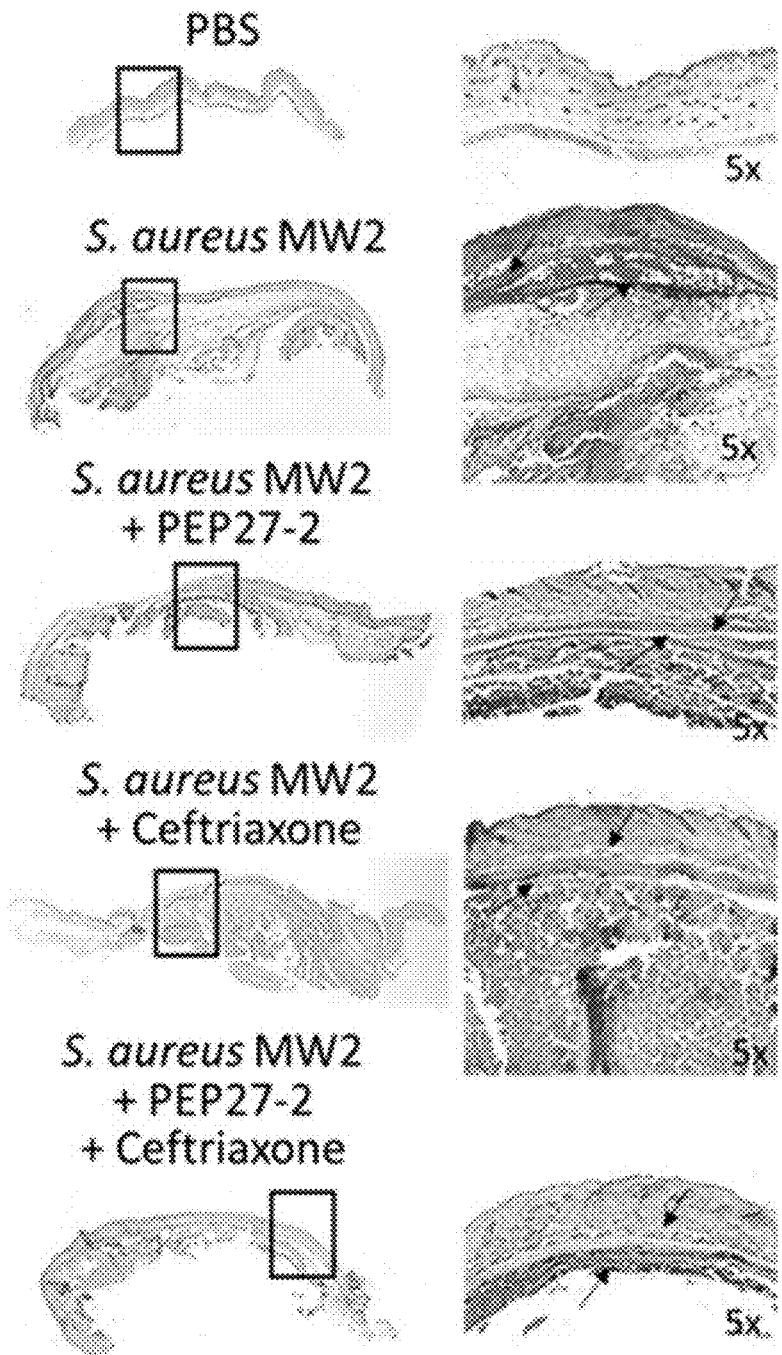
FIG. 9 illustrates results of confirming a change in abscess tissues when PEP27 peptide and antibiotics, that is, ceftriaxone, respectively, are used alone or in combination with the same for treatment of abscess formed after infection with *Staphylococcus aureus* MW2 which is a multidrug-tolerant strain.

As a result, the infected portion of a mouse infected with *Staphylococcus aureus* MW2 alone was extended from the skin tissue to the deep skeletal muscle tissue, and neutrophils and macrophages were observed around the infected portion. Due to deep inflammation in the upper dermis, damage and necrosis of skeletal muscles, a large abscess with shells/scabs was formed on the top of the skin (FIG. 9). By counting the number of bacteria and live fluorescence imaging, it was confirmed that *Staphylococcus aureus* MW2 with increased scabs was contained in the skin surface. On 2 hours after infection of *Staphylococcus aureus* MW2, the mice were treated with PEP27-2, ceftriaxone or a combination thereof, respectively. From the treated mice, it was confirmed that the number of visible scabs formed on the skin surface and the number of bacteria were markedly reduced. However, it was confirmed that inflammatory response occurred most noticeably in the tissue fragment during the combination treatment (FIG. 9).

18. Analysis of Pro-Inflammatory Cytokine Gene Expression Using Quantitative Real-Time PCR mRNA expression of inflammatory mediators such as tumor necrosis factor-alpha (TNF-α), interleukin-1 beta (IL-1β), interleukin-6 (IL-6), nitrogen oxide synthetase (iNOS) and cyclooxygenase-2 (COX-2) is changed during skin infection and wound healing. For mice not infected with bacteria, infected mice, and mice subjected to treatment using PEP27-2 alone, ceftriaxone alone or a combination thereof after infection, the expression of inflammatory genes in the mice were measured thus to verify the efficacy of each of PEP27-2 single treatment and combination treatment with antibiotics.

Specifically, total RNA was isolated from wound tissues using Trizol reagent. From the prepared total RNA, cDNA was synthesized using a cDNA synthesis kit. qPCR was implemented using qPCR 2× premix (SYBR Green), followed by determining expression amounts of TNF-α, IL-1β, IL-6, iNOS and COX-2 among inflammatory genes. Expression levels were quantified based on β-actin, and the PCR process was conducted as followed: at 50° C. for 2 minutes and at 95° C. for 10 minutes; 95° C. for 15 seconds, 60° C. for 1 minute, 40 cycles; 95° C. for 15 seconds, 60° C. for 1 minute, 95° C. for 30 seconds, and 60° C. for 15 seconds. The gene expression was calculated after standardization to β-actin level through ΔΔCt method. Transcription of the control cell was set to 1 and other experimental groups have multiple of the set value.

Figure 10:
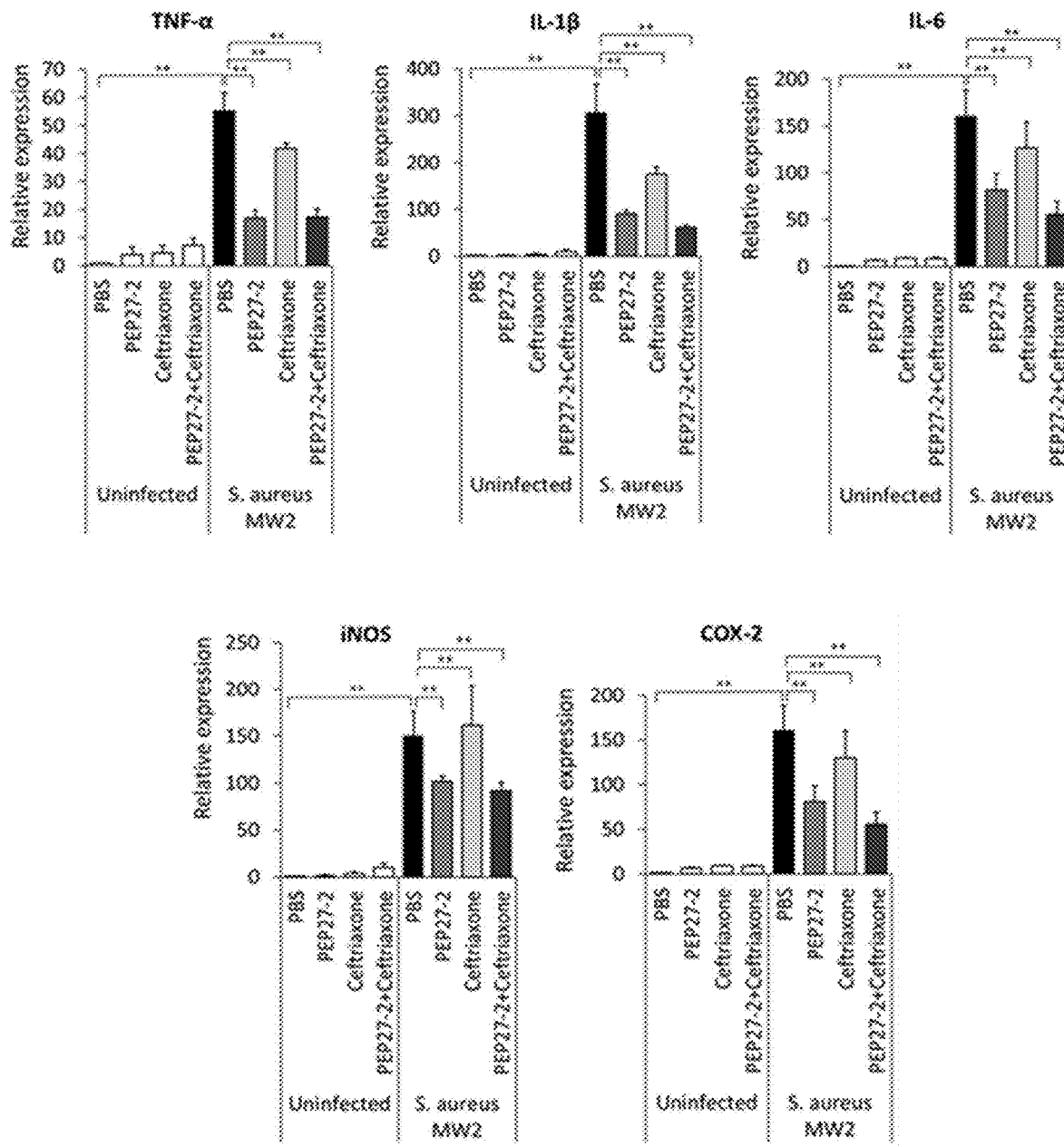
FIG. 10 illustrates results of confirming the relative expression rate of genes related to inflammatory response in abscess tissues formed after infection with *Staphylococcus aureus* MW2 which is a multidrug-tolerant strain (TNF-α: tumor necrosis factor-alpha, IL-1R: interleukin-1 beta, IL-6: interleukin-6, iNOS: nitrogen oxide synthetase, COX-2: cyclooxygenase-2).

As a result of confirming the expression of TNF-α, IL-1β, IL-6, iNOS and COX-2, it was observed that the expression of each of the inflammatory cytokines was increased in the abscess portion of the skin infected with *Staphylococcus aureus* MW2 strain. Further, in the conditions in which the skin wounds infected with bacteria were subjected to PEP27-2 single treatment, ceftriaxone single treatment or combination treatment thereof, it was confirmed that the expression of inflammatory cytokines was suppressed (FIG. 10). Further, the combination treatment of PEP27-2 and ceftriaxone exhibited stronger suppression of the inflammatory cytokines than the single treatment using either thereof except for TNF-α. On the other hand, in the case of TNF-α, PEP27-2 single treatment and combination treatment of PEP27-2 and ceftriaxone, the expression was similarly suppressed. This result was demonstrated that the combination treatment had synergistic effects in suppressing the expression of some inflammatory mediators derived from the mouse infected with *Staphylococcus aureus* MW2. Therefore, it was confirmed that, when PEP27-2 is combined with ceftriaxone injection, antimicrobial effects against *Staphylococcus aureus* MW2 would be exhibited in vivo, thereby inhibiting inflammation occurring in response to infection.

From the above experimental results, it could be confirmed that three types of PEP27 analogs (SEQ ID NOS: 2 to 4) according to the present invention had low cytotoxicity to normal cells, and exhibited antimicrobial activity to gram-positive bacteria, gram-negative bacteria and antibiotics-tolerant bacteria, which is substantially excellent than or equal to that of PEP27 as the parental peptide. Specifically, among the synthesized peptides, PEP27-2 peptide (SEQ ID NO: 3) was demonstrated to exhibit remarkably excellent antimicrobial activity compared to the PEP27 parental peptide. In addition, when the synthetic peptide analog is used for treatment in combination with antibiotics, it was confirmed that synergistic effects could be obtained for antimicrobial activity to the gram-positive bacteria, gram-negative bacteria and antibiotics-tolerant bacteria.

Preparative Example 1: Preparation of Pharmaceutical Formulation 1-1. Preparation of Powder

TABLE 10

| Component | Weight (mg) |
| --- | --- |
| Peptide of the present invention | 20 mg |
| Lactose | 20 mg |

After admixing the above components, the mixture was filled in an airtight cloth bag to prepare powder.

1-2. Preparation of Tablets

| Component | Weight (mg) |
| --- | --- |
| Peptide of the present invention | 10 mg |
| Corn starch | 100 mg |
| Lactose | 100 mg |
| Magnesium stearate | 2 mg |

After admixing the above components, the mixture was punched to form a tablet formulation according to the conventional tablet formation method.

1-3. Preparation of Capsules

TABLE 12

| Component | Weight (mg) |
|---|---|
| Peptide of the present invention | 10 mg |
| Crystalline cellulose | 3 mg |
| Lactose | 14.8 mg |
| Magnesium stearate | 0.2 mg |

After admixing the above components, the mixture was charged in a gelatin capsule to form a capsule formulation according to the conventional capsule preparation method.

1-4. Preparation of Liquid Formulation

TABLE 13

| Component | Weight (mg) |
|---|---|
| Peptide of the present invention | 20 mg |
| Isomerized sugar | 10 g |
| Mannitol | 5 g |
| Purified water | Appropriate amount |

According to the conventional preparation method of liquid preparation, each of the components was added to purified water to dissolve it, followed by adding lemon zest in an appropriate amount and blending the above components, then, purified water was added to adjust a total amount to 100 ml. Thereafter, the mixture was charged in a brown bottle, followed by sterilization thus to prepare the liquid formulation.

1-5. Preparation of Injection Formulation

TABLE 14

| Component | Addition amount |
|---|---|
| Peptide of the present invention | 10 mg/ml |
| Diluted hydrochloric acid BP | Till reaching pH 7.6 |
| Main sodium chloride BP | Max. 1 ml |

The peptide of the present invention was dissolved in an appropriate volume of the main sodium chloride BP for primary use, the pH of the resulting solution was adjusted to pH 7.6 with diluted hydrochloric acid BP, and the volume was adjusted with the main sodium chloride BP and then sufficiently blended. The solution was charged in a 5 ml type I ampoule made of transparent glass, the glass was dissolved and air-sealed under an upper grid, followed by sterilizing the same in an autoclave at 120° C. for 15 minutes or longer, thereby preparing an injection formulation.

Preparative Example 2: Preparation of Cosmetics

2-1. Emollient Lotion (Skin)

In order to prepare an antimicrobial emollient skin lotion containing the peptide of the present invention, the following components could be admixed as listed in Table 15 below to prepare the emollient skin lotion according to the conventional manufacturing method in the field of cosmetics.

TABLE 15

| Component | Content (wt. %) |
|---|---|
| Peptide of the present invention | 0.1 to 30 |
| 1,3-butyleneglycol | 3.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | Trace amount |
| Flavor | Trace amount |
| Purified water | To 100 |

2-2. Nutritional Lotion (Lotion)

In order to prepare an antimicrobial nutritional lotion containing the peptide of the present invention, the following components could be admixed as listed in Table 16 below to prepare the nutritional lotion according to the conventional manufacturing method in the field of cosmetics.

TABLE 16

| Component | Content (wt. %) |
|---|---|
| Peptide of the present invention | 0.1 to 30 |
| Squalane | 10.0 |
| Polyoxyethylene sorbitan monooleate | 2.0 |
| Guaiacum oil | 0.1 to 30 |
| 1,3-butyleneglycol | 8.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | Trace amount |
| Flavor | Trace amount |
| Purified water | To 100 |

2-3. Essence

In order to prepare an antimicrobial essence containing the peptide of the present invention, the following components could be admixed as listed in Table 17 below to prepare the essence according to the conventional manufacturing method in the field of cosmetics.

TABLE 17

| Component | Content (wt. %) |
|---|---|
| Peptide of the present invention | 0.1 to 30 |
| Sitosterol | 1.7 |
| Polyglyceryl 2-oleate | 1.5 |
| Ceramide | 0.7 |
| Ceteares-4 | 1.2 |
| Cholesterol | 1.5 |
| Dicetyl phosphate | 0.4 |
| Concentrated glycerin | 5.0 |
| Carboxylvinyl polymer | 0.2 |
| Xanthan gum | 0.2 |
| Preservative | Trace amount |

TABLE 17-continued

| Component | Content (wt. %) |
| --- | --- |
| Flavor | Trace amount |
| Purified water | To 100 |

2-4. Face Wash (Cleansing Foam)

In order to prepare an antimicrobial face wash (cleansing foam) containing the peptide of the present invention, the following components could be admixed as listed in Table 18 below to prepare the cleansing foam according to the conventional manufacturing method in the field of cosmetics.

TABLE 18

| Component | Content (wt. %) |
| --- | --- |
| Peptide of the present invention | 0.1 to 30 |
| Sodium N-acylglutamate | 20.0 |
| Glycerin | 10.0 |
| PEG-400 | 15.0 |
| Propyleneglycol | 10.0 |
| POE(15) oleylalcohol ether | 3.0 |
| Laurin derivative | 2.0 |
| Methyl paraben | 0.2 |
| EDTA-4Na | 0.03 |
| Flavor | 0.2 |
| Purified water | To 100 |

2-5. Nourishing Cream

In order to prepare an antimicrobial nutrient cream containing the peptide of the present invention, the following components could be admixed as listed in Table 19 below to prepare the nourishing cream according to the conventional manufacturing method in the field of cosmetics.

TABLE 19

| Component | Content (wt. %) |
| --- | --- |
| Peptide of the present invention | 0.1 to 30 |
| Vaseline | 7.0 |
| Liquid paraffin | 10.0 |
| Beewax | 2.0 |
| Polysorbate 60 | 2.5 |
| Sorbitan sesquioleate | 1.5 |
| Squalane | 3.0 |
| Propyleneglycol | 6.0 |
| Glycerin | 4.0 |
| Triethanolamine | 0.5 |
| Xanthan gum | 0.5 |
| Tocopherol acetate | 0.1 |
| Flavor, preservative | Trace amount |
| Purified water | To 100 |

2-6. Massage Cream

In order to prepare an antimicrobial massage cream containing the peptide of the present invention, the following components could be admixed as listed in Table 20 below to prepare the massage cream according to the conventional manufacturing method in the field of cosmetics.

TABLE 20

| Component | Content (wt. %) |
| --- | --- |
| Peptide of the present invention | 0.1 to 30 |
| Propyleneglycol | 6.0 |
| Glycerin | 4.0 |
| Triethanolamine | 0.5 |
| Beewax | 2.0 |
| Tocophenyl acetate | 0.1 |
| Polysorbate 60 | 3.0 |
| Sorbitan sesquioleate | 2.5 |
| Cetearyl alcohol | 2.0 |
| Liquid paraffin | 30.0 |
| Xanthan gum | 0.5 |
| Flavor, preservative | Trace amount |
| Purified water | To 100 |

2-7. Pack

In order to prepare an antimicrobial pack containing peptide of the present invention, the following components could be admixed as listed in Table 21 below to prepare the pack according to the conventional manufacturing method in the field of cosmetics.

TABLE 21

| Component | Content (wt. %) |
| --- | --- |
| Peptide of the present invention | 0.1 to 30 |
| Propyleneglycol | 2.0 |
| Glycerin | 4.0 |
| Polyvinyl alcohol | 10.0 |
| Ethanol | 7.0 |
| PiG-40 hydrogenated castor oil | 0.8 |
| Triethanolamine | 0.3 |
| Flavor, preservative | Trace amount |
| Purified water | To 100 |

REFERENCE TO AN ELECTRONIC SEQUENCE LISTING

A sequence listing electronically submitted with the present application on Jun. 15, 2023 as XML file named 20230615_Q73822LC09-V_TU_SEQ.XML, created on Jun. 13, 2023 and having a size of 8,564 bytes, is incorporated herein by reference in its entirety.

What is claimed is:

1. A method of killing or reducing a growth of methicillin-resistant *Staphylococcus aureus* (*S. aureus*), the method comprising:
   administering a composition comprising a peptide consisting of the amino acid sequence of SEQ ID NO:2 or 3 to a subject in need thereof.

2. The method of claim 1, wherein the methicillin-resistant *Staphylococcus aureus* (*S. aureus*) is *S. aureus* MW2.

3. The method of claim 1, wherein the composition further comprises at least one antibiotic selected from the group consisting of meropenem, ceftazidim and ceftriaxone.

4. A method for treating an abscess comprising:
   administering a composition comprising a peptide consisting of the amino acid sequence of SEQ ID NO:2 or 3 to a subject in need thereof,
   wherein the abscess is formed after infection with *Staphylococcus aureus* MW2.

* * * * *